United States Patent
Toth et al.

(10) Patent No.: US 11,998,172 B2
(45) Date of Patent: Jun. 4, 2024

(54) ENDOSCOPE AND METHOD OF USE

(71) Applicant: Meditrina, Inc., San Jose, CA (US)

(72) Inventors: Akos Toth, Cupertino, CA (US); Csaba Truckai, Saratoga, CA (US)

(73) Assignee: Meditrina, Inc., San Jose, CA (US)

( * ) Notice: Subject to any disclaimer, the term of this patent is extended or adjusted under 35 U.S.C. 154(b) by 94 days.

(21) Appl. No.: 16/677,411

(22) Filed: Nov. 7, 2019

(65) Prior Publication Data

US 2020/0138271 A1    May 7, 2020

Related U.S. Application Data

(60) Provisional application No. 62/756,979, filed on Nov. 7, 2018.

(51) Int. Cl.
| | |
|---|---|
| *A61B 1/00* | (2006.01) |
| *A61B 1/018* | (2006.01) |
| *A61B 1/05* | (2006.01) |
| *A61B 1/06* | (2006.01) |

(52) U.S. Cl.
CPC ...... *A61B 1/00114* (2013.01); *A61B 1/00018* (2013.01); *A61B 1/05* (2013.01); *A61B 1/06* (2013.01); *A61B 1/018* (2013.01); *A61B 1/051* (2013.01)

(58) Field of Classification Search
CPC ......... A61B 1/00114; A61B 1/05; A61B 1/06; A61B 1/04; A61B 1/51
See application file for complete search history.

(56) References Cited

U.S. PATENT DOCUMENTS

| | | | | |
|---|---|---|---|---|
| 5,003,273 A | * | 3/1991 | Oppenberg | H05K 1/0219 |
| | | | | 174/117 FF |
| 5,300,899 A | * | 4/1994 | Suski | H05K 1/0253 |
| | | | | 174/254 |
| 5,334,800 A | * | 8/1994 | Kenney | H05K 1/0224 |
| | | | | 174/250 |
| 5,682,124 A | * | 10/1997 | Suski | H01P 3/085 |
| | | | | 174/254 |
| 5,766,167 A | | 6/1998 | Eggers et al. | |
| 6,259,846 B1 | | 7/2001 | Roach et al. | |
| 6,281,451 B1 | * | 8/2001 | Chan | H01B 7/0861 |
| | | | | 174/268 |

(Continued)

FOREIGN PATENT DOCUMENTS

| | | | |
|---|---|---|---|
| CN | 106658948 A | * | 5/2017 |
| JP | H6-269408 | | 9/1994 |
| WO | WO 2020/097361 | | 5/2020 |

*Primary Examiner* — John P Leubecker
(74) *Attorney, Agent, or Firm* — Levine Bagade Han LLP

(57) ABSTRACT

An endoscope includes a shaft having proximal and distal ends and a longitudinal axis therebetween. A handle is coupled to the proximal end of the shaft, and an image sensor is carried on the distal end of the shaft. A channel extends through at least a distal shaft portion and has a channel diameter, and a section of the channel is re-configurable between a constricted shape and a non-constricted shape to accommodate tools introduced therethrough. The combined diagonal dimension and channel diameter is usually greater than the outer shaft diameter. The image sensor may be connected to a connector on the housing by a first slack flex circuit and a lights source on the shaft may be connected to a connector on the housing by a second slack flex circuit.

12 Claims, 18 Drawing Sheets

(56) References Cited

U.S. PATENT DOCUMENTS

| | | | | |
|---|---|---|---|---|
| 6,444,921 | B1* | 9/2002 | Wang | H01L 23/4985 439/91 |
| 6,614,325 | B1* | 9/2003 | Kocin | H05K 1/0245 174/251 |
| 8,858,425 | B2* | 10/2014 | Farr | A61B 90/37 600/110 |
| 11,324,116 | B2* | 5/2022 | Han | H05K 3/361 |
| 2006/0109368 | A1 | 5/2006 | Ayrenschmalz | |
| 2006/0110110 | A1* | 5/2006 | Yi | G02B 6/4292 385/33 |
| 2011/0103028 | A1* | 5/2011 | Malo | G06F 1/1633 361/753 |
| 2011/0118549 | A1* | 5/2011 | Han | A61B 1/04 29/854 |
| 2012/0065469 | A1* | 3/2012 | Allyn | A61B 1/005 600/109 |
| 2012/0126828 | A1* | 5/2012 | Cohen | A61B 5/05 324/629 |
| 2014/0009593 | A1* | 1/2014 | Segi | A61B 1/051 29/745 |
| 2014/0071646 | A1* | 3/2014 | Qian | H05K 3/4644 174/250 |
| 2014/0249368 | A1* | 9/2014 | Hu | A61B 1/0011 600/109 |
| 2014/0320617 | A1* | 10/2014 | Parks | A61B 1/045 348/65 |
| 2016/0037027 | A1* | 2/2016 | Elliott, Jr. | A61B 1/0058 348/76 |
| 2016/0351292 | A1 | 12/2016 | Toth et al. | |
| 2017/0035277 | A1* | 2/2017 | Kucharski | A61B 1/018 |
| 2017/0042615 | A1* | 2/2017 | Salahieh | A61B 5/6858 |
| 2018/0168437 | A1 | 6/2018 | Schreiner et al. | |
| 2018/0206712 | A1* | 7/2018 | Begg | A61B 1/00183 |
| 2019/0089875 | A1* | 3/2019 | Fan | A61B 1/051 |
| 2019/0150711 | A1* | 5/2019 | Chiu | A61B 1/00105 |

* cited by examiner

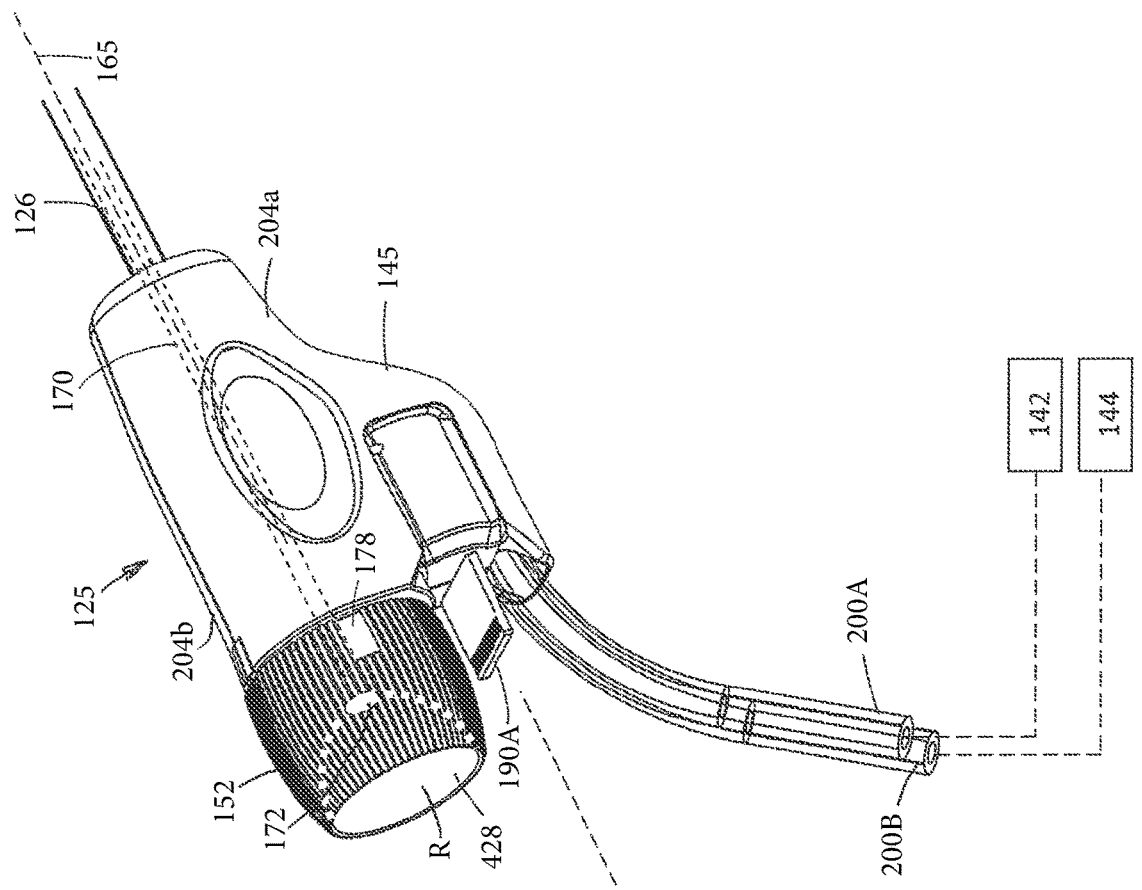
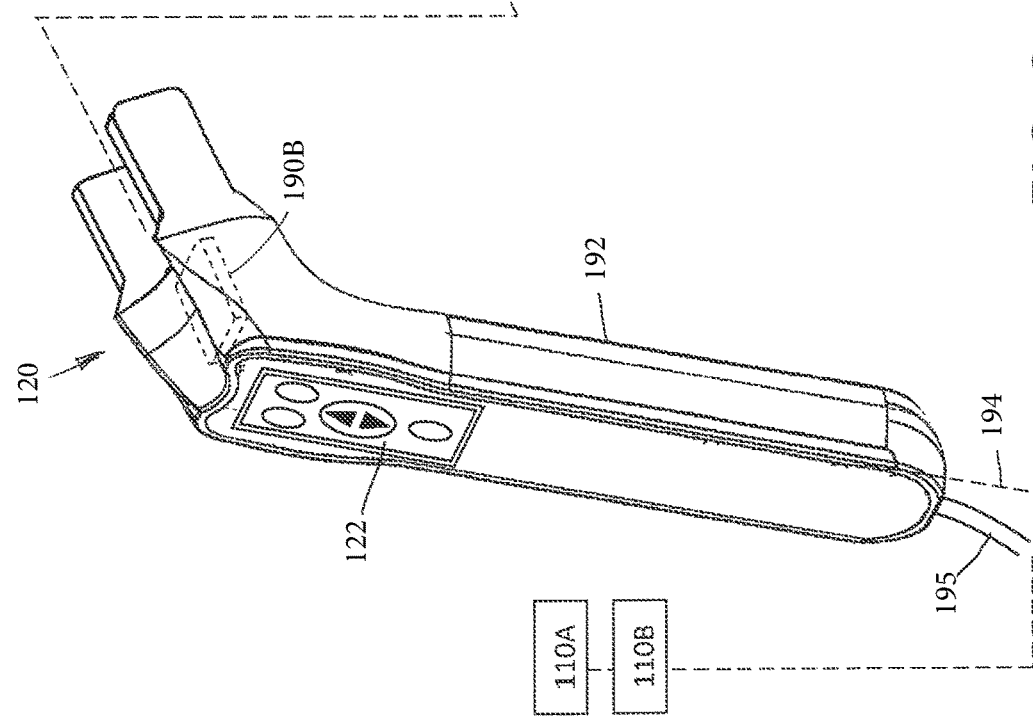
FIG. 2

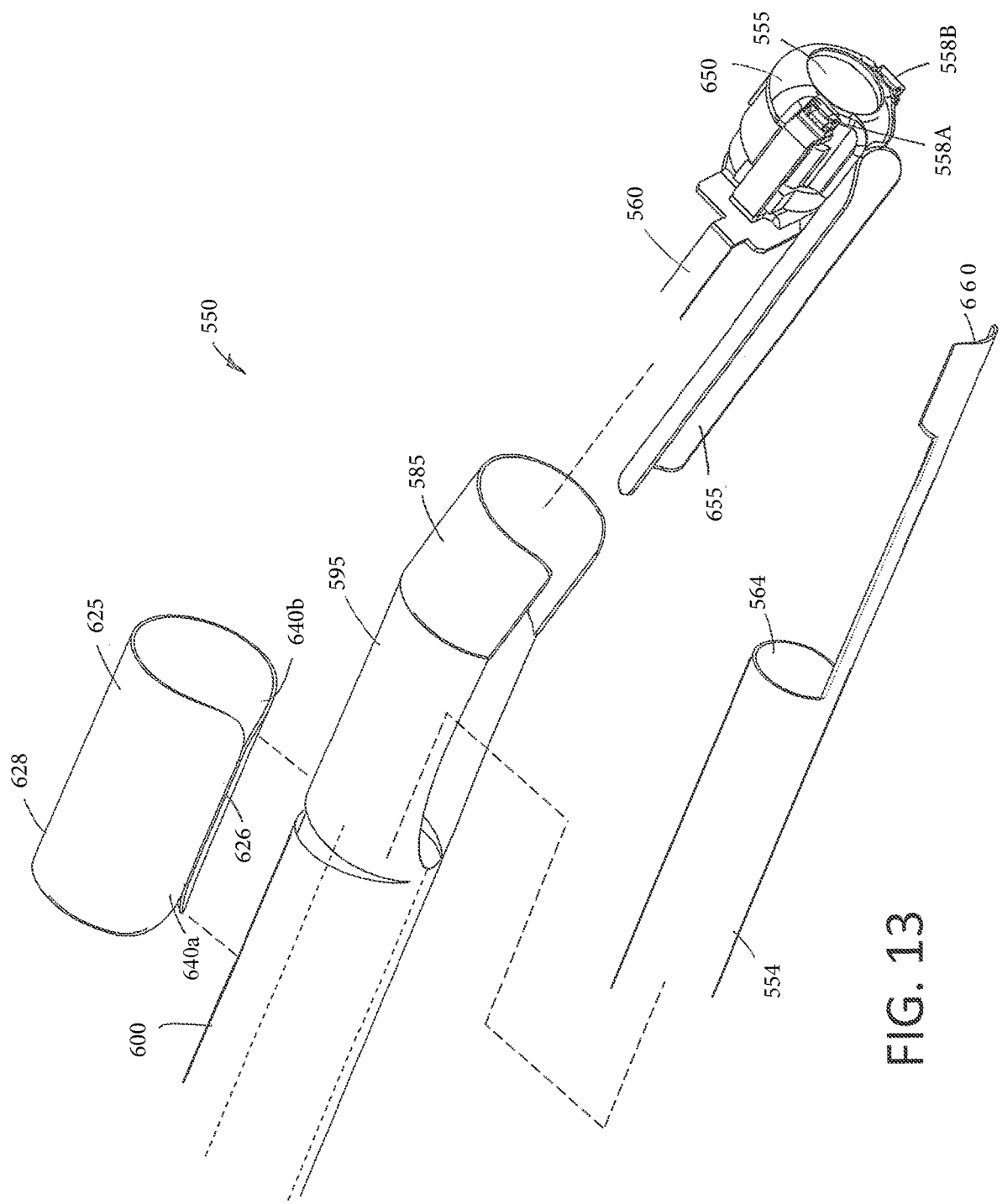

ENDOSCOPE AND METHOD OF USE

RELATED APPLICATION

This is a non-provisional application of U.S. Provisional 62/756,979 filed Nov. 7, 2018, the entirety of which is incorporated by reference herein.

BACKGROUND OF THE INVENTION

The present invention relates generally to medical devices and methods. More particularly, the present invention is related to endoscopic systems suitable for hysterectomy and other purposes.

Endoscopic systems of the invention intended for hysterectomy typically comprise a base station having an image display, a disposable endoscope component with an image sensor, a re-usable handle component that is connected to an image processor in the base station, and a fluid management system integrated with the base station and handle component. The endoscope component and the re-useable handle are typically referred to as a hysteroscope.

Of particular interest to the present invention, hysteroscopes and other endoscopes provide for the introduction of interventional tools through a working channel in the shaft of the scope. The size of the working channel of a hysteroscope is limited by the need to introduce at least a distal portion of the shaft through the patient's cervix.

Of further interest to the present invention, hysteroscopes may have a shaft rotatable relative to the handle, and that shaft will often carry a camera and light source that need to be externally connected through the handle.

Of still further interest to the present invention, rotatable hysteroscope shafts may also carry fluids through a lumen which has an external port fixed in the handle.

For these reasons, it would be desirable to provide improved hysteroscopes which can accommodate the introduction of comparatively large tools through a shaft with a relatively low profile. It would be further desirable to provide improved hysteroscopes which can accommodate the connection of cameras, light sources, and the like, on rotatable shafts through stationary handles. It would be still further desirable to provide improved hysteroscopes which can accommodate the flow of fluids through rotatable shafts coupled to stationary handles. At least some of these objectives will be met by the inventions described hereinbelow. However, the methods and devices described herein will include additional benefits as recited by the claims.

Hysteroscopic systems of a type similar to that illustrated herein are described in commonly owned, co-pending application Ser. Nos. 15/712,603; 15/836,460; 15/861,474; and 15/975,626, the full disclosures of which are incorporated herein by reference.

SUMMARY OF THE INVENTION

The present disclosure includes endoscopes as well as components for use in endoscopes. For example, in one variation, the present disclosure includes a flexible circuit for an endoscope configured for use in a fluid environment. For example, such a flexible circuit can comprise an elongated flexible circuit extending in a planar shape to a distal end; an image sensor operatively coupled to a surface of the flex circuit and a first arrangement of electrical conductors therein; an illumination source operatively coupled to a surface of the flex circuit and a second arrangement of electrical conductors therein; and wherein said first arrangement of electrical conductors is disposed in an interior of the flex circuit with a superior dielectric layer and an inferior dielectric layer sufficient to prevent electrical coupling through both of the superior dielectric layer and the inferior dielectric layer to prevent interference with an image sensor signal carried by the first arrangement of electrical conductors.

In one variation, the flexible circuit includes superior and inferior dielectric layers each comprise a polymeric layer having a thickness of at least 0.0508 mm (0.002") and up to 0.1016 mm (0.004"). The superior and inferior dielectric layers can comprise any ide suitable polymer, such as a polyamide.

In an additional variation, the circuit includes a second arrangement of electrical conductors disposed in an interior of the flex circuit with superior and inferior dielectric layers sufficient to prevent electrical coupling therethrough.

In an additional variation, the image sensor and the illumination source are coupled to a distal portion of the flexible circuit member in a first repose spaced apart configuration and is configured for deformation to dispose the image sensor and illumination source in a second spaced apart configuration for coupling to a distal portion of an elongated endoscope shaft. The flexible circuit member can have a planar shape in said first configuration and a non-planar shape in said second configuration.

Variations of the flexible circuit include a first segment of the flexible circuit carrying the image sensor is configured for deformation from the planar shape to dispose the image sensor adjacent a proximal end of a lens assembly carried by the endoscope shaft. The second segment of the flexible circuit carrying the illumination source can be configured for deformation to dispose the illumination source proximate to a distal end of the lens assembly. The first segment can include a first flex region with increased flexibility for flexing away from said planar shape. Alternatively, or in combination, the second segment can include a second flex region with increased flexibility for flexing away from said planar shape.

Another variation of a flexible circuit for an endo scope, includes an elongated flexible circuit extending in a planar shape to a distal end having first and second flex elements adapted to bend away from the planar shape; an image sensor with a field of view axis operatively coupled to a surface of the first flex element; an illumination source with a light axis operatively coupled to a surface of the second flex element; wherein the first and second flex elements are capable of bending away from the planar shape to a non-planar shape for coupling to an endoscope shaft where the field of view axis and light axis are in a distal-facing orientation; wherein the image sensor has a plurality of electrical contacts coupled to corresponding electrical conductors in the flexible circuit; and wherein said electrical conductors are disposed in an interior of the flex circuit with superior and inferior dielectric layers sufficient to prevent electrical coupling through said dielectric layers to thereby prevent interference with image sensor signals carried by said electrical conductors.

The illumination source discussed herein can comprise an incandescent light, an LED, an illumination source that radiates non-visible light, as well as any light transmitting material (e.g., a fiber) that transmits light from an illumination source.

The descriptions provided herein are examples of the invention described herein. It is contemplated that combinations of specific embodiments, specific aspects or combinations of the specific embodiments themselves are within the scope of this disclosure.

BRIEF DESCRIPTION OF THE DRAWINGS

Additional aspects of the invention will become clear from the following description of illustrative embodiments and from the attached drawings, in which:

FIG. 2 is perspective view of the endoscopic viewing system of FIG. 1 showing a single-use disposable endoscope component separated from a reusable handle component.

FIG. 13 is an exploded view of the components of the endoscope working end of FIGS. 11, 12A and 12B.

FIG. 14 is an exploded view showing the insulator layers in a conductive layer layers of the flex circuit in a plane are form showing the multiple leads that connect to the image sensor and the LEDs.

DETAILED DESCRIPTION OF THE INVENTION

Figure 1:
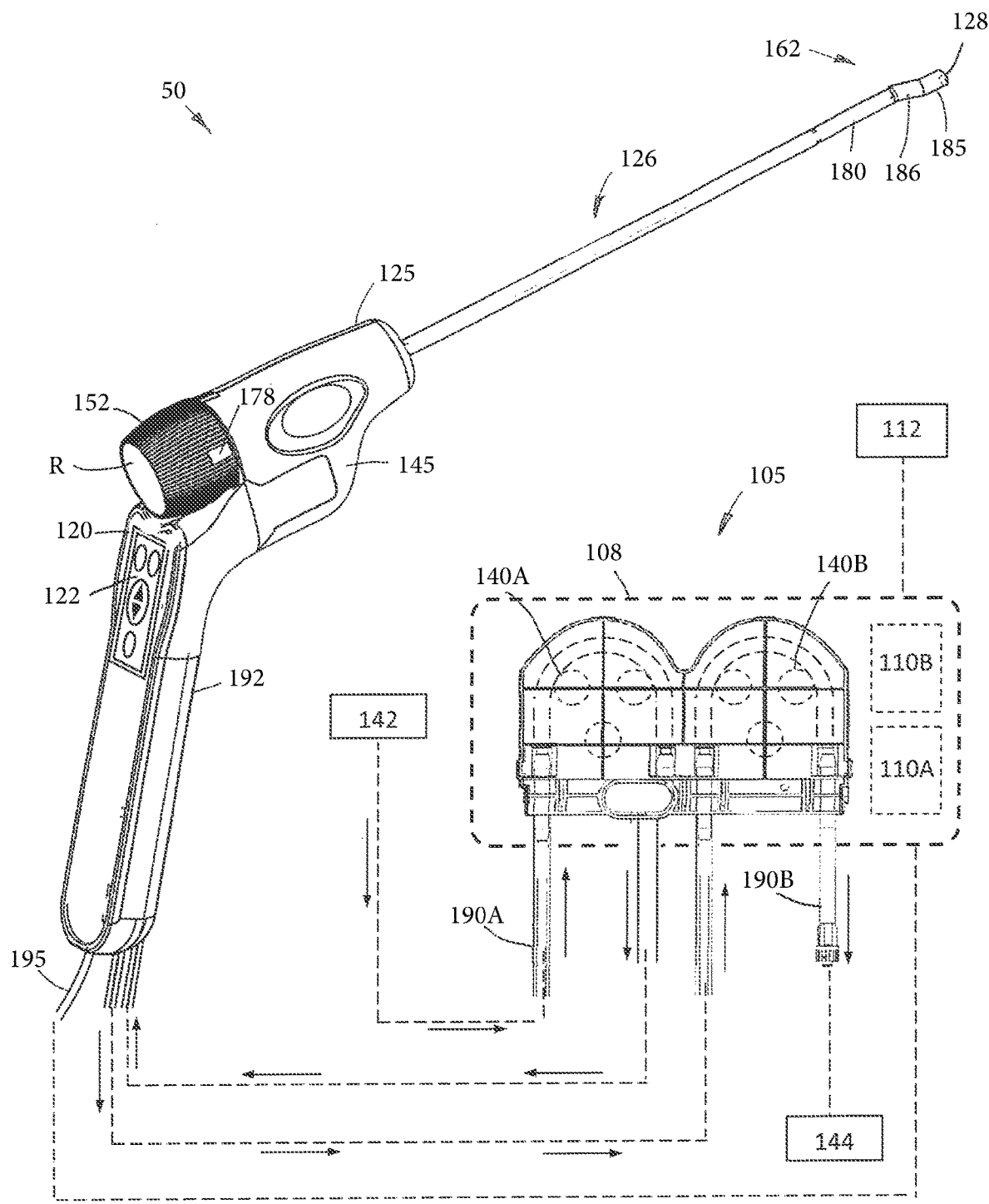
FIG. 1 illustrates components of a hysteroscopic treatment system corresponding to the invention, including a perspective view of an endoscopic viewing system and a schematic view of a fluid management system.

FIG. 1 illustrates a hysteroscopic treatment system 50 corresponding to the invention which comprises multiple components including an endoscopic viewing system 100 and a fluid management system 105 housed in a base unit or console 108. The base unit 108 also carries a controller 110A and power source for operating the system 50 and can include an image processor 110B for processing signals from an image sensor carried by the endoscopic viewing system. A display 112 can be coupled to the base unit 108 for viewing images provided by the endoscopic viewing system 100.

Figure 7A:
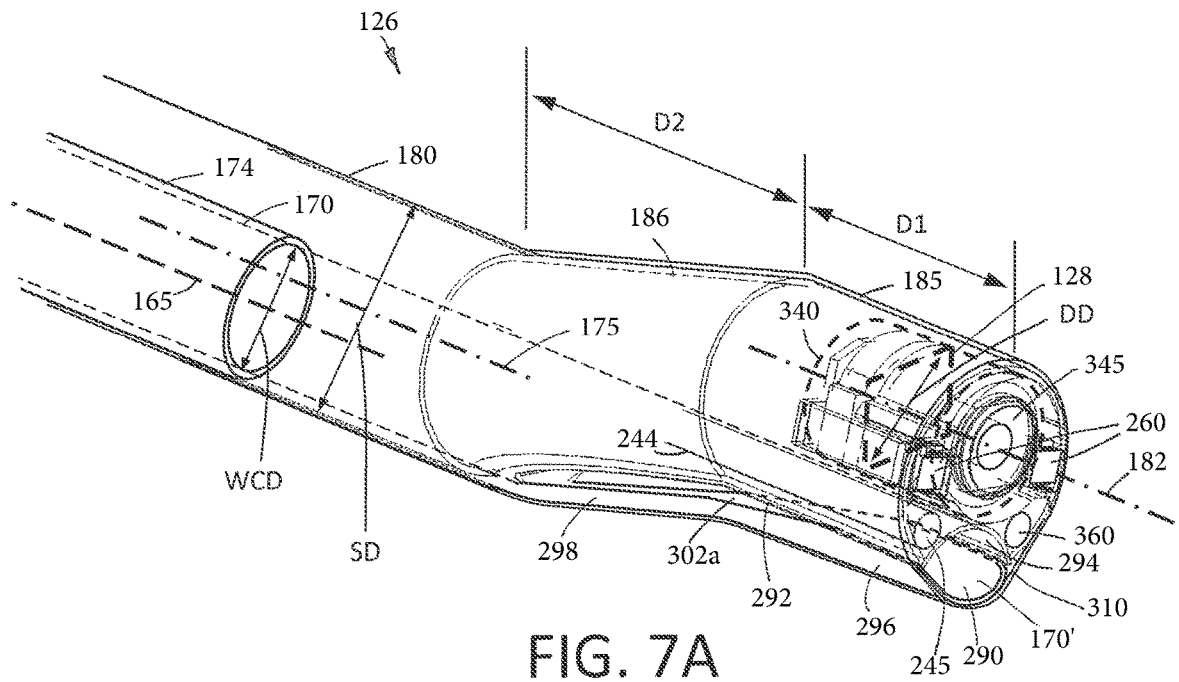
FIG. 7A is an enlarged perspective view of the distal end of the endoscope shaft showing the working channel with a distal channel portion in a reduced cross-sectional configuration for introduction into a patient's body.

More in particular, the endoscopic viewing system 100 of FIGS. 1 and 2 includes a re-usable handle component 120 with a finger-actuated control pad 122 and a disposable single-use endoscope component 125 with an elongated endoscope shaft 126 that carries a distal electronic imaging sensor 128 (see FIGS. 1 and 7A). The fluid management system 105 includes a first peristaltic inflow pump 140A and second peristaltic outflow pump 140B, a fluid source 142 and fluid collection reservoir 144 which can include a fluid deficit measurement subsystem as is known in the art. Each of the systems and subsystems will be described in more detail below.

Figure 3A:
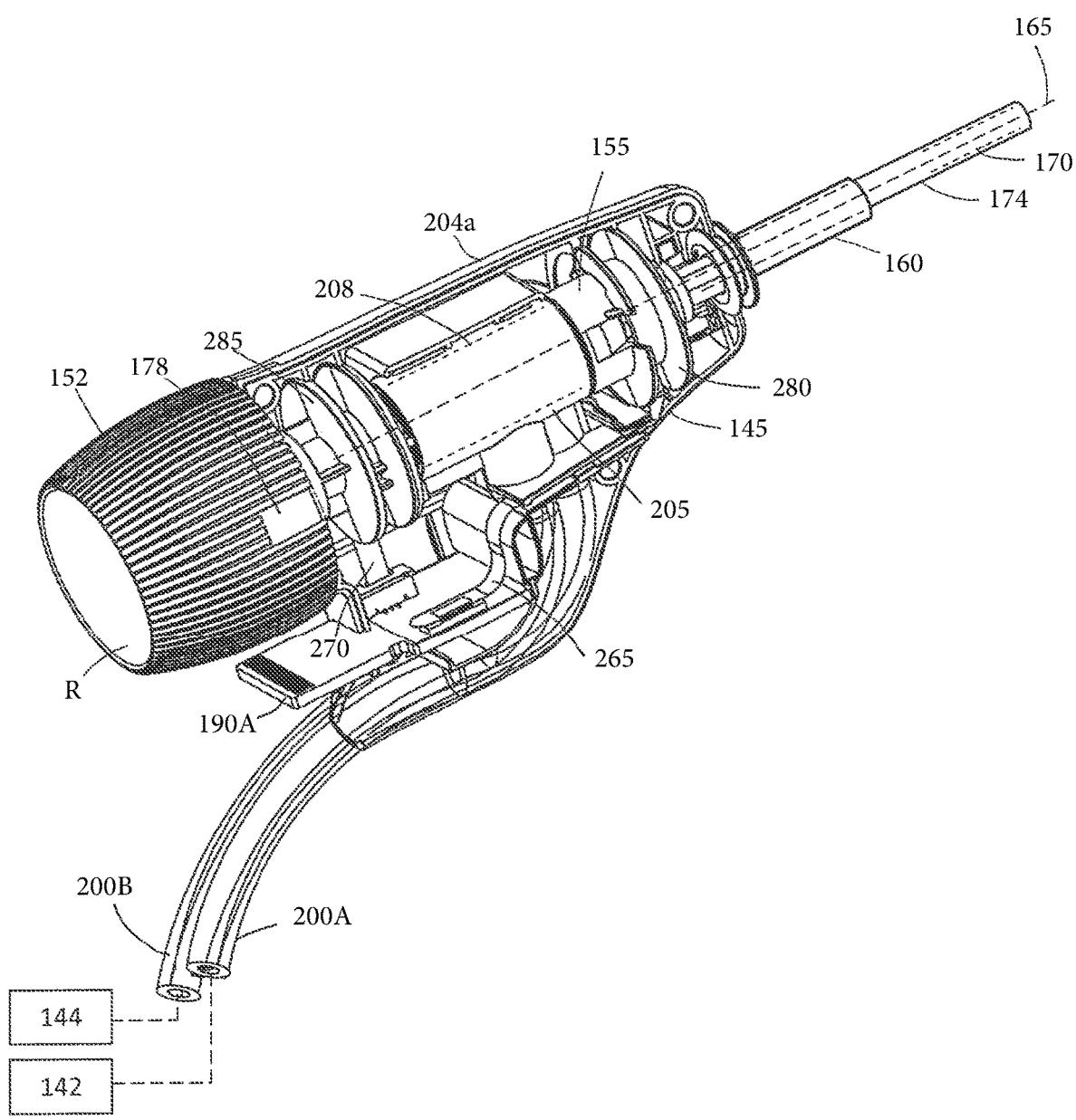
FIG. 3A is perspective view of single-use endoscope component of FIG. 2 with the handle shell partially removed to show an interior portion of the component.
Figure 3B:
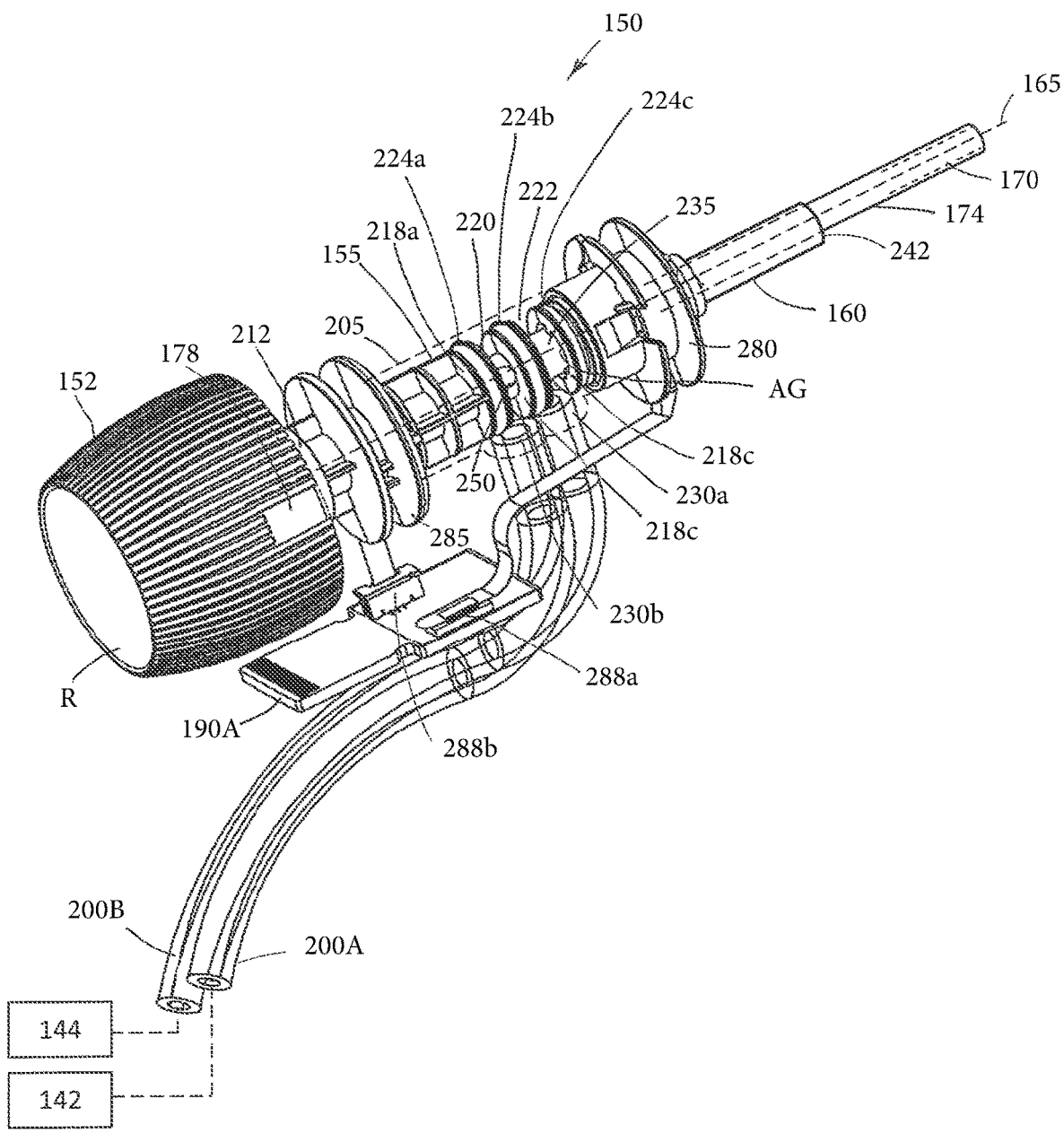
FIG. 3B is perspective view of endoscope component of FIG. 3A with a flow channel housing removed to show features of a rotating shaft assembly.

Referring to FIGS. 1, 2 and 3B, it can be seen that the endoscopic viewing system 100 includes a handle component 120 and a detachable single-use endoscope component 125. In FIG. 2, the single-use endoscope component 125 can be seen as an assembly of a proximal handle housing 145 which carries a rotating shaft assembly 150 that is configured to rotate the handle housing 145.

Figure 4:
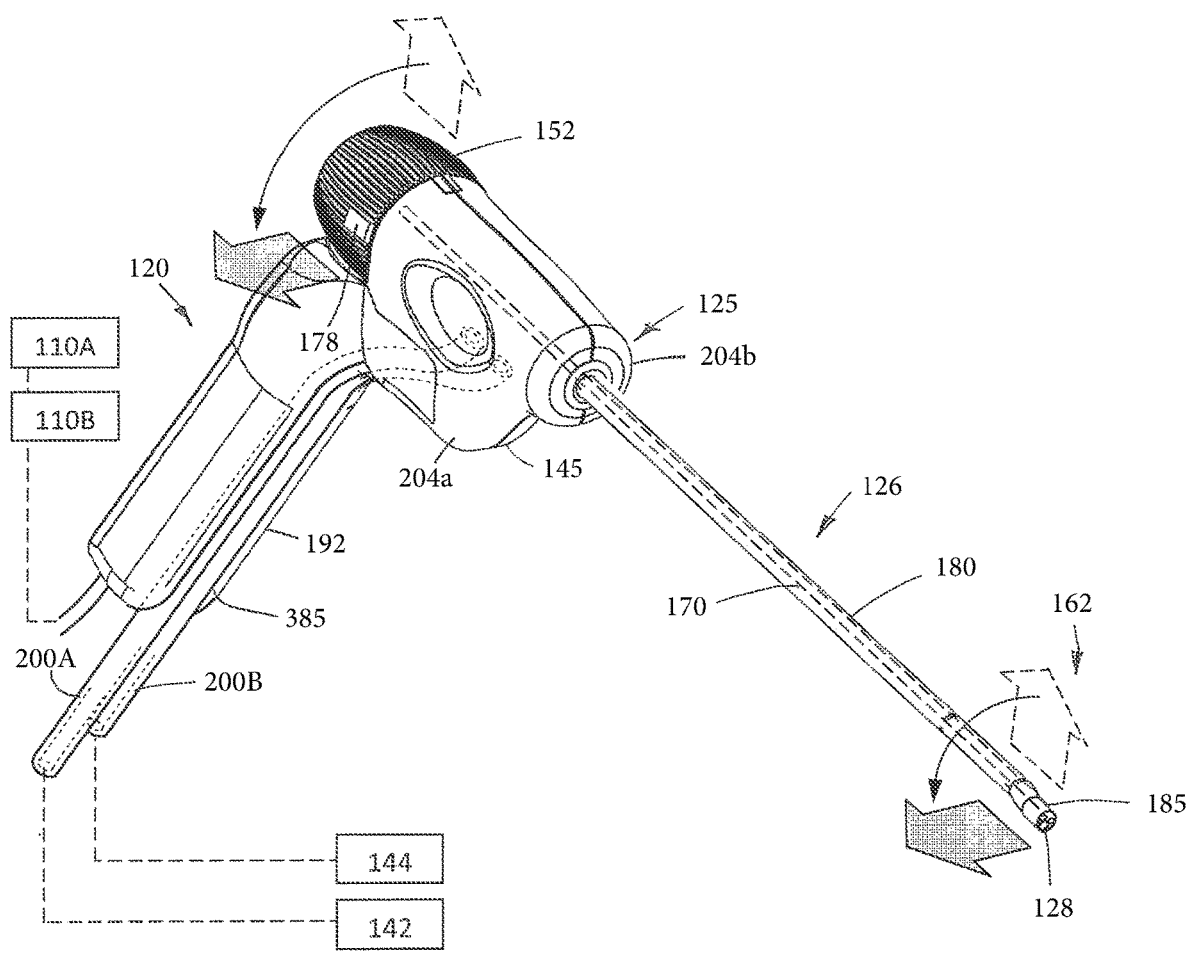
FIG. 4 is a perspective view of the endoscopic viewing system of FIG. 1 from a different angle illustrating rotation of the rotating shaft assembly.
Figure 5:
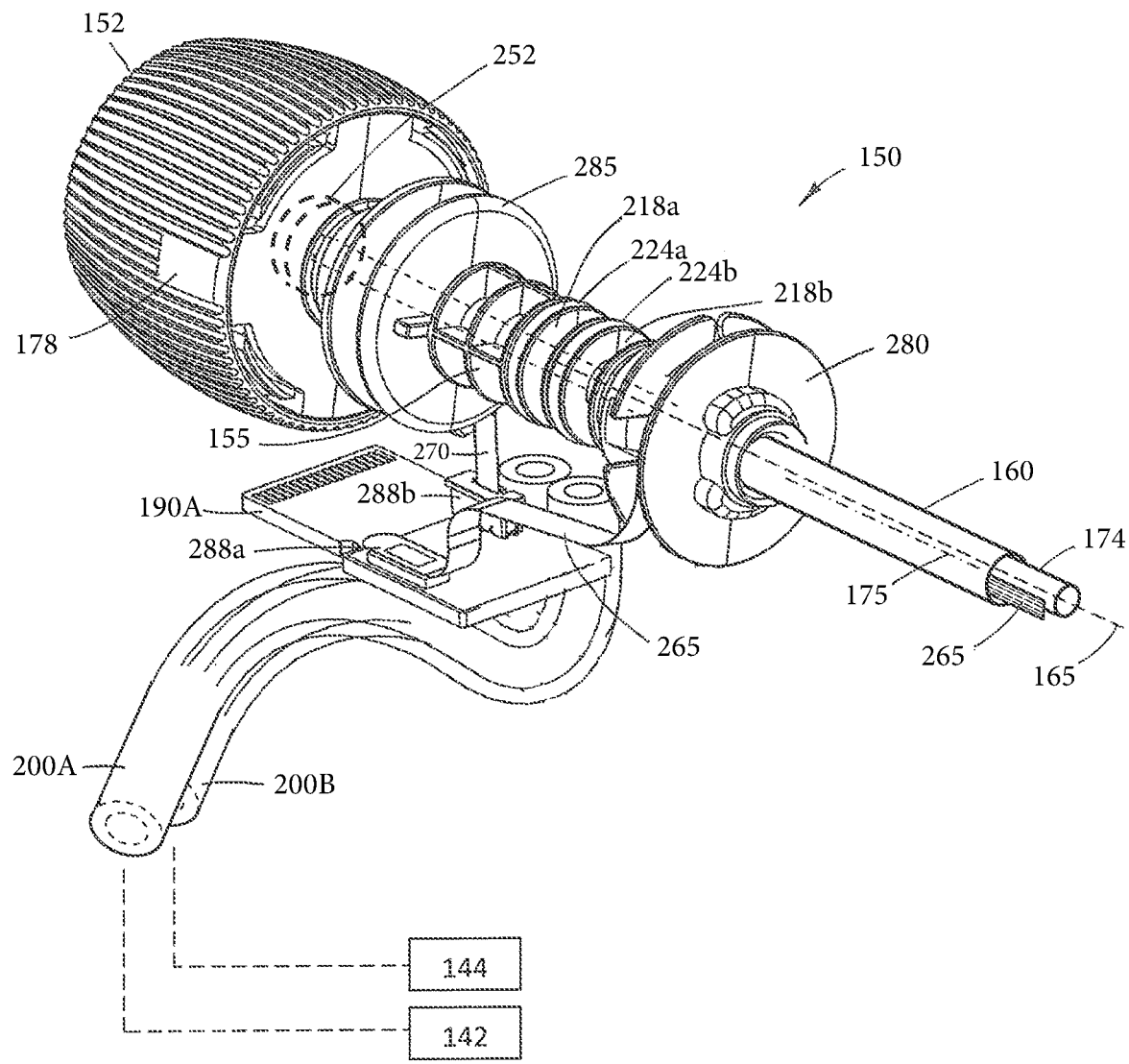
FIG. 5 is another perspective and sectional view of endoscope component of FIGS. 3A-3B with a flow channel housing removed to show the central axis of the working channel around which the shaft assembly rotates and the off-center longitudinal axis of the outer sleeve of the endoscope shaft.

Referring to FIGS. 1, 3B and 5, the rotating shaft assembly 150 includes a proximal cylindrical grip 152 that is coupled to a molded rotating core 155 that in turn is coupled to elongated outer sleeve 160 that extends to the distal working end 162 the endoscope component 125 (FIG. 1). The rotating shaft assembly 150 rotates around a rotational axis 165. A working channel 170 extends about axis 165 through the rotating shaft assembly 150 from a proximal port 172 (see FIGS. 2 and 6). The working channel sleeve 174 that carries the working channel 170 can be seen in FIGS. 3A, 3B and 5. Thus, the shaft assembly 150 rotates about the central longitudinal axis 165 of the working channel 170. As can be seen in FIGS. 5 and 7A, the outer sleeve 160 has a central longitudinal axis 175 that is offset from the longitudinal axis 165 around which the shaft assembly 150 rotates. FIG. 4 shows that the grip 152 has a visual marker 178 that is aligned with the offset distal tip section 185 to allow the operator to know the orientation of the image sensor 128 by observation of the grip 152.

In FIGS. 1, 4, 6 and 7A, it can be seen that the endoscope shaft 126 and more particularly the outer sleeve 160 extends in a straight proximal sleeve portion 180 to an offset distal tip section 185 with an axis 182 that is also from 2 to 10 mm offset from the central axis 175 of the outer sleeve 160 (FIG. 7A). The outer sleeve 160 has a transition section 186 that extends at an angle ranging between 10° and 45° over a length of 5 to 20 mm between the straight proximal sleeve section 180 and the offset distal tip section 185. The imaging sensor 128 is disposed at the distal end of the offset tip section 185 (see FIG. 7A). As can be seen in FIGS. 5 and 7B, the endoscope component 125 and more in particular the working channel 170 is adapted to receive an elongate tool 188 that can be introduced through the working channel 170. In one variation, the elongated outer sleeve 160 in each of the straight, transition and distal tip sections (180, 186 and 185, respectively) has a diameter ranging between 4 mm and 10 mm with an overall length configured for use in hysteroscopy. More commonly, the diameter of endoscope shaft 126 is from 5 mm to 6 mm in diameter. It has been found that the endoscope shaft 126 with the angled transition section 186 and offset distal tip section 185 can be introduced through a patient's cervical canal without dilation beyond the dilation necessary for the profile or diameter SD of the straight proximal sleeve section 180. In other words, the tissue around the patient's cervical canal conforms to the angles in the endoscope shaft 126 as the shaft is being advanced through the cervical canal.

In one variation, the handle housing 145 of endoscope component 125 is adapted for sliding, detachable engagement with the handle component 120 as can be best seen in FIGS. 2 and 4. As can be easily understood, when assembled, the operator can grip the pistol grip handle component 120 with one hand and rotate the cylindrical rotating grip 152 with the fingers of the other hand to rotate the endoscope shaft and image sensor 128 to orient the viewing angle of the image sensor 128 and a tool 188 to any desired rotational angle. As will be described below, the rotating shaft assembly 150 can be rotated at least 180° and more often at least 270° (FIGS. 3B and 5). In one variation, the shaft assembly 150 can be rotated 360° so as to orient the image sensor 128 in any superior, lateral or downward direction relative to the handle housing 145.

As can be seen in FIG. 2, the handle housing 145 carries a projecting electrical connector 190A that is adapted to couple to a mating electrical connector 190B in the handle component 120. While FIG. 2 illustrates that the endoscope component 125 is configured for axial sliding engagement with the handle component 120, it should be appreciated that the angled pistol grip portion 192 of the handle component 120 could plug into the endoscope component 125 in a different arrangement, such as a male-female plug connector or a threaded connector aligned with the axis 194 of the angled grip portion 192. As will be described below, the endoscope component 125 comprises a sterile device for use in the sterile field, while the handle component 120 may not be sterilized and is typically adapted for use for use in a non-sterile field. A cable 195 extends from the handle component 120 to the base unit 108, imaging processor 110B and controller 110A which includes a power source (see FIG. 1).

As can be seen in FIGS. 1 and 2, the endoscope component 125 includes fluid inflow tubing 200A and fluid outflow tubing 200B that communicate with the fluid management system 105 which is shown schematically in FIG. 1. As can be understood from FIGS. 2, 3A and 3B, the endoscope handle housing 145 can consist of two injection molded plastic shell elements, 204a and 204b (see FIG. 4), and FIG. 3A shows one shell element 204a removed to show the interior of the handle housing 145. It can be seen that both the inflow tubing 200A and outflow tubing 200B are coupled to an injection molded flow channel housing 205 with an interior bore 208 that is configured to receive a rotating core 155 of the rotating shaft assembly 150.

FIG. 3B is another view similar to that of FIG. 3A with the second shell element 204b removed and the flow channel housing 205 also removed (phantom view) to illustrate how the stationary inflow and outflow tubing, 200A and 200B, communicate with the inflow and outflow pathways in the rotating shaft assembly 150 which rotates at least 180°.

Referring to FIGS. 3A and 3B, it can be seen that the rotating core 155 is centrally aligned with the axis 165 of working channel 170 and is further coupled to the off-center elongated outer sleeve 160 of the endoscope shaft 126. The proximal end 212 of the rotating core 155 is fixed to the grip 152 for rotating the rotating core 155 in the flow channel housing 205.

The rotating core 155 includes first, second and third flanges 218a, 218b and 218c which define annular flow channels 220 and 222 therebetween. It can be seen that annular channel 220 is disposed between the first and second flanges 218a and 218b. Annular channel 222 is disposed between the second and third flanges 218b and 218c. Each of the first, second and third flanges 218a, 218b and 218c carry an outer O-ring 224a, 224b and 224c. From the views of FIGS. 3A and 3B, it can be understood how the rotating flanges 218a-218c rotate in the bore 208 of the flow channel housing 205 and the O-rings 224a-224c maintain a fluid tight seal between the annular flow channels 220 and 222.

Again referring FIGS. 3A and 3B, it can be seen that the distal end 230a of inflow tubing 200A is fixed in the flow channel housing 205 to communicate with annular flow channel 222. Similarly, the distal end 230b of outflow tubing 200B is fixed in the flow channel housing 205 to communicate with annular flow channel 220. Thus, each of the annular flow channels 222 and 220 can rotate up to 360° and communicate with the stationary distal ends of the inflow tubing 200A and outflow tubing 200B.

FIG. 3B further shows how the annular flow channels 222 in 220 communicate with separate flow pathways that extend through the interior of the elongated sleeve 160 to the working end 162 of the endoscope shaft 126. The fluid inflow pathway can be seen in FIG. 3B which extends through annular gaps AG around the exterior of inner sleeve portion 235 of the rotating core 155 within the second annular channel 222. Such annular gaps AG extend distally to communicate with the interior bore 242 of the outer sleeve 160. In one variation, the pathway within said interior bore 242 transitions to the inflow sleeve 244 with distal outlet 245 as shown in FIGS. 7A-7B.

The fluid outflow pathway also can be seen in FIG. 3B wherein an opening 250 is provided in the inner surface of annular space 220 of the rotating core 155 which communicates with the interior working channel 170. Thus, the outflow pathway from a working space in one variation comprises the working channel 170 which is fully open for fluid outflows when there is no tool 188 in the working channel. In FIG. 5, it can be seen that a tool seal 252 is shown in the proximal region of the working channel 170 that seals the channel 170 and also permits the tool 188 to be introduced therethrough. Many types of seals are known such in the art as silicone sleeve seals, flap seals and the like.

Typically, when a tool is introduced through the working channel 170, the tool itself will provide an outflow channel. Thus, the use of the working channel 170 as outflow passageway is adapted for diagnostic procedures when using the endoscope without a tool in the working channel.

In a method of use, the endoscope shaft 126 can be navigated through a patient's end cervical canal with the inflow and outflow pumps 140A and 140B (see FIG. 1) operating to provide continuous irrigation through the distal tip section 185 of the endoscope component 125 together with endoscopic viewing by means of image sensor 128. Such a variation will thus allow fluid inflows through annular channel 222 and fluid outflows through the working channel 170 and annular channel 220.

Now turning to FIGS. 7A-7B, the endoscope shaft 126 has a small insertion profile or configuration that consists of the outer diameter of the elongated outer sleeve 160 which includes the proximal straight section 180, the angled transition section 186 and the distal tip section 185 (FIG. 7A). It can be seen in FIG. 7A that the distal tip section 185 carries an image sensor 128 and two LEDs 260 which require an electrical connection to base unit 108, the controller 110A and imaging processor 110B. In order to provide the large number of electrical leads required for the image sensor 128, it was found that conventional multi-wire electrical cables were too large to be accommodated by the small diameter outer sleeve 160 which also accommodates working channel 170, an inflow channel 244 and potentially other fluid flow channels. For this reason, it was found that a printed flex circuit in the form of a flat ribbon 265 (FIG. 5) could provide from 10 to 40 electrical leads and occupy only a thin planar space within the endoscope shaft 126. FIG. 7A shows the flex circuit ribbon 265 extending from the image sensor 128 proximally within outer sleeve 160. In one variation shown in FIGS. 3A, 3B, 5 and 7A, a second flex circuit ribbon 270 is provided to power the LEDs 260. In another variation, the first flex circuit ribbon 265 could potentially carry electrical leads to the image sensor 128 and to the two LEDs 260.

Now turning to FIGS. 3A, 3B and 5, mechanisms are illustrated that provide for needed slack in the electrical circuitry or flex circuit ribbons 265 and 270 for accommodating rotation of the rotating shaft assembly 150 relative to the handle housing 145 (FIG. 3A). As can best be seen in FIGS. 3B and 5, the rotating shaft assembly 150 includes a first or distal spool 280 around which the flex circuit ribbon 265 can be coiled or spooled. The distal spool 280 is formed as a part of the rotating core 155 of the rotating shaft assembly 150. Any suitable length of the flex circuit ribbon 265 can be provided as needed to allow for at least 180° rotation, or more often, 360° of rotation of the rotating shaft assembly 150 relative to the handle housing 145. In the variation shown in FIGS. 3B and 5, it can be seen that a second or proximal spool 285 comprises a portion of the rotating core 155 and is adapted for receiving a slack length of the second flex circuit ribbon 270 that extends to the two LEDs 260. In FIGS. 3B and 5, it can be seen that the proximal ends 265', 270' of the flex circuit ribbons 265, 270 are coupled to electrical connector 190A by plug connector 288a and 288b. While the variation of FIGS. 3A-3B shows the endoscope handle accommodating the flex circuit ribbon 265 in a spool 280, it should be appreciated that the slack portion of the flex circuit ribbon can be configured with at least one of a coiled form, spiral form or folded form without a spool.

In one aspect of the invention, referring to FIG. 7A, an endoscope shaft 126 is provided that carries a distal image sensor 128 wherein the diameter of a working channel 170 in the shaft 126 is greater than 50% of the outer diameter of the shaft 126 and the electrical leads to the image sensor 128 comprise the flex circuit 265. In such a variation, the flex circuit ribbon has a thickness of less than 0.4 mm and a width of less than 5.0 mm. More often, the flex circuit ribbon has a thickness of less than 0.3 mm and a width of less than 4.0 mm. Further, in this variation, the flex circuit ribbon carries at least 10 electrical leads of often more than 15 electrical leads. In another aspect, electrical leads extending to the image sensor 128 are in a cable or ribbon that has a cross-section that is less than 5% or the cross-section of the endoscope shaft 126. In another aspect of the invention, the endoscope comprises a shaft carrying a distal image sensor, a working channel extending through the shaft wherein the working channel in a distal shaft portion is re-configurable between a constricted shape and a non-constricted shape to accommodate a tool introduced therethrough, wherein the combined diagonal dimension DD of the sensor and the diameter WCD of the working channel 170 is greater than the shaft diameter SD in its insertion configuration or profile (see FIGS. 4, 6 and 7A).

In a specific example, the image sensor 128 is available from OmniVision, 4275 Burton Drive, Santa Clara, CA 95054 with the part name/number: High Definition Sensor OV9734 with a 1280×720 pixel count. The sensor 128 has package dimensions of 2532 μm×1722 μm, with a diagonal DD of 3062 μm or 3 mm. Further, the proximal shaft (outer) diameter SD is 5 mm with the working channel diameter WCD being 3 mm. Thus, the combined sensor diagonal DD (3 mm) and the working channel diameter WCD (3 mm) equals 6 mm which is greater than the outer shaft diameter of 5 mm. In this example, the flex circuit ribbon is 3.4 mm in width and 0.2 mm thickness with a cross-sectional area of 0.68 mm$^2$ which is 3.52% of the 5 mm diameter shaft having a cross-sectional area of 19.63 mm$^2$. In this specific variation, the flex circuit ribbon 265 carries 19 electrical leads.

Referring again to FIGS. 7A-7B, the distal portion of the endoscope shaft 126 includes a distal working channel portion 170' that is re-configurable between a first smaller cross-section as shown in FIG. 7A for accommodating fluid outflows and a second larger cross-section as shown in FIG. 7B for accommodating a tool 188 introduced through the working channel 170 and its distal portion 170'.

In one variation as shown in FIGS. 3A-3B, 5, 6, and 7A, it can be seen that the working channel sleeve 174 that defines working channel 170 extends in a straight configuration through the endoscope component 125 from its proximal opening port 172 to its open distal termination 290. As can be seen in FIGS. 7A and 7B, the distal end 292 of sleeve 174 has a superior surface 294 that is straight and rigid. The working channel sleeve 174 has an inferior or lower sleeve portion 296 that is flexible and in one variation has a living hinge portion 298 below sidewall cut-outs 302a and 302b in the sleeve 174. Further, the distal end of the endoscope shaft 126 includes an elastomeric sleeve 310 that surrounds the angled transition sleeve section 186, the distal tip section 185 as well as a distal portion 312 of the proximal straight sleeve section 180 (FIG. 7B). Thus, as can be seen in FIG. 7A, the elastomeric sleeve 310 has sufficient elastic strength to collapse or constrict the working channel portion 170' to the smaller cross-section as seen in FIG. 7A.

As can be seen in FIG. 7A, the lower sleeve portion 296 includes a sleeve wall 315 with sufficient curvature to maintain an open pathway through the distal working channel portion 170' when the elastomeric sleeve 310 constricts the distal channel portion 170' which thereby always provides an open fluid outflow pathway. For example, the sleeve wall 315 can have a curvature representing the same diameter as a proximal portion of sleeve 174 and extend over a radial angle ranging from 30° to 90°. While the lower sleeve portion 296 shown in FIG. 7A comprises a portion of the wall of metal sleeve 174, in another variation, the flexible lower sleeve portion 296 may be any bendable plastic material or a combination of plastic and metal.

FIG. 7B next shows the distal working channel portion 170' in its second expanded configuration as when a physician inserts an elongated tool 188 (phantom view) through the working channel 170. Such a tool 188 will initially slide along the hinge portion 298 of the lower sleeve portion 296 and then stretch the elastomeric sleeve 310 to open distal working channel portion 170' to allow the tool 188 to extend through the working channel. In other words, the elastomeric sleeve 310 will be stretched or deformed to a tensioned position as shown in FIG. 7B as a tool is inserted through the distal working channel portion 170'. When the tool 188 is withdrawn from the working channel portion 170', the elastomeric sleeve 310 will return from the tensioned position of FIG. 7B to the repose or non-tensioned position of FIG. 7A to return the working channel portion 170' to the constricted configuration FIG. 7A.

In general, the endoscope component 125 corresponding to the invention allows for the use of an image sensor 128 having a large diagonal dimension relative to the insertion profile or diameter of the endoscope shaft 126 while at the same time providing a working channel 170 that has a large working channel diameter WCD relative to the insertion profile or diameter of the endoscope shaft assembly 126. More in particular, the endoscope component 125 comprises endoscope shaft 126 having a shaft diameter SD extending to a distal sleeve section 185, an image sensor 128 with a diagonal dimension DD carried by the distal sleeve section 185 and a working channel 170 having a diameter WCD extending through the elongated shaft 126, wherein the working channel portion 170' in the distal end of the shaft 126 is adjustable in shape to accommodate a tool 188 introduced therethrough and wherein the combination or the sensor's diagonal dimension DD and the working channel diameter WCD is greater than the shaft diameter SD (see FIG. 7A).

In a variation, the sensor diagonal dimension DD is greater than 50% of the shaft diameter SD or greater than 60% of the shaft diameter. In a variation, the working channel diameter WCD is greater than 30% of the shaft diameter, greater than 40% of the shaft diameter or greater than 50% of the shaft diameter. In other words, the working channel portion 170' in the distal end is adjustable between a first cross-sectional dimension and a second cross-section dimension. In the variation of FIGS. 7A-7B, the working channel portion 170' in the distal region of the endoscope shaft 126 is adjustable between a partially constricted shape and a non-constricted shape.

In one variation, referring to FIG. 7A, the distal tip section 185 of the endoscope shaft 126 has an axial dimension D1 ranging from 5 mm to 20 mm. Also referring to FIG. 7A, the angled transition sleeve section 186 extends over a similar axial dimension D2 ranging from 5 mm to 20 mm. Still referring to FIG. 7A, the central axis 182 of distal tip section 185 can be parallel to and offset from the longitudinal axis 175 of the straight shaft section 180 by a distance ranging from 1 mm to 10 mm.

Figure 7B:
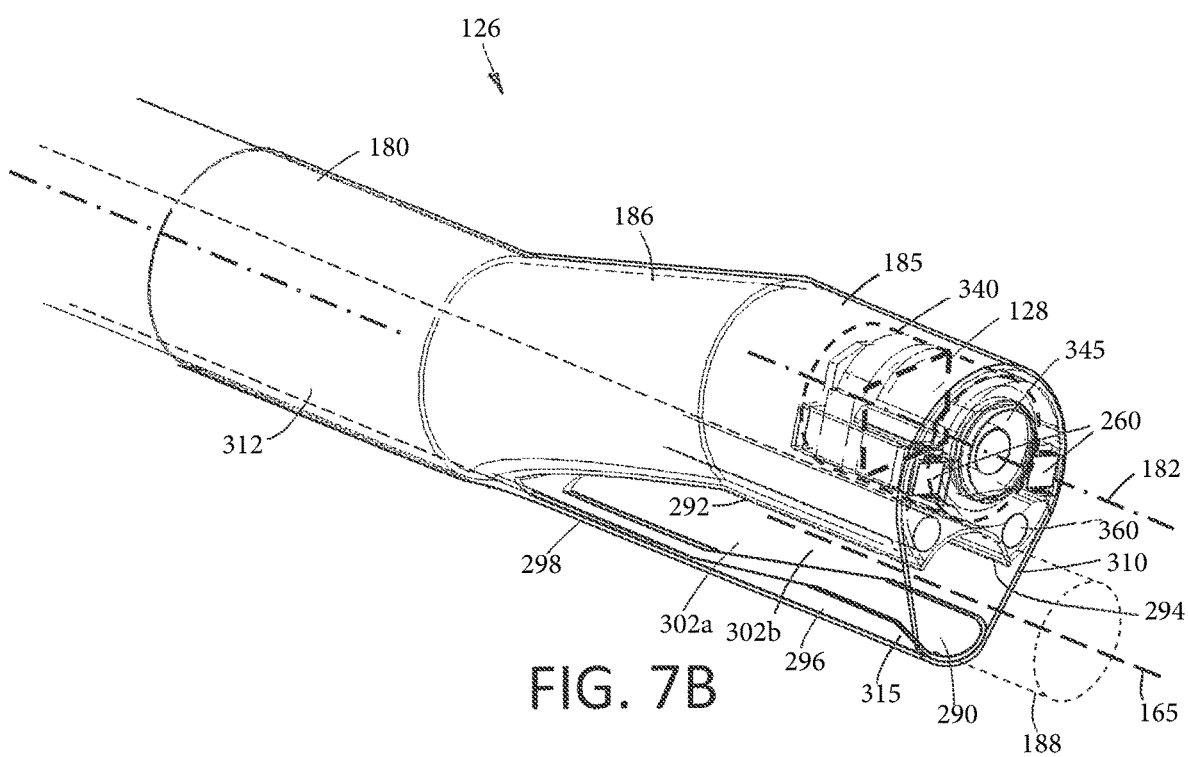
FIG. 7B is another view of the distal end of the endoscope shaft of FIG. 7A showing the distal working channel portion in an expanded cross-sectional configuration when a tool is introduced through the working channel.
Figure 8:
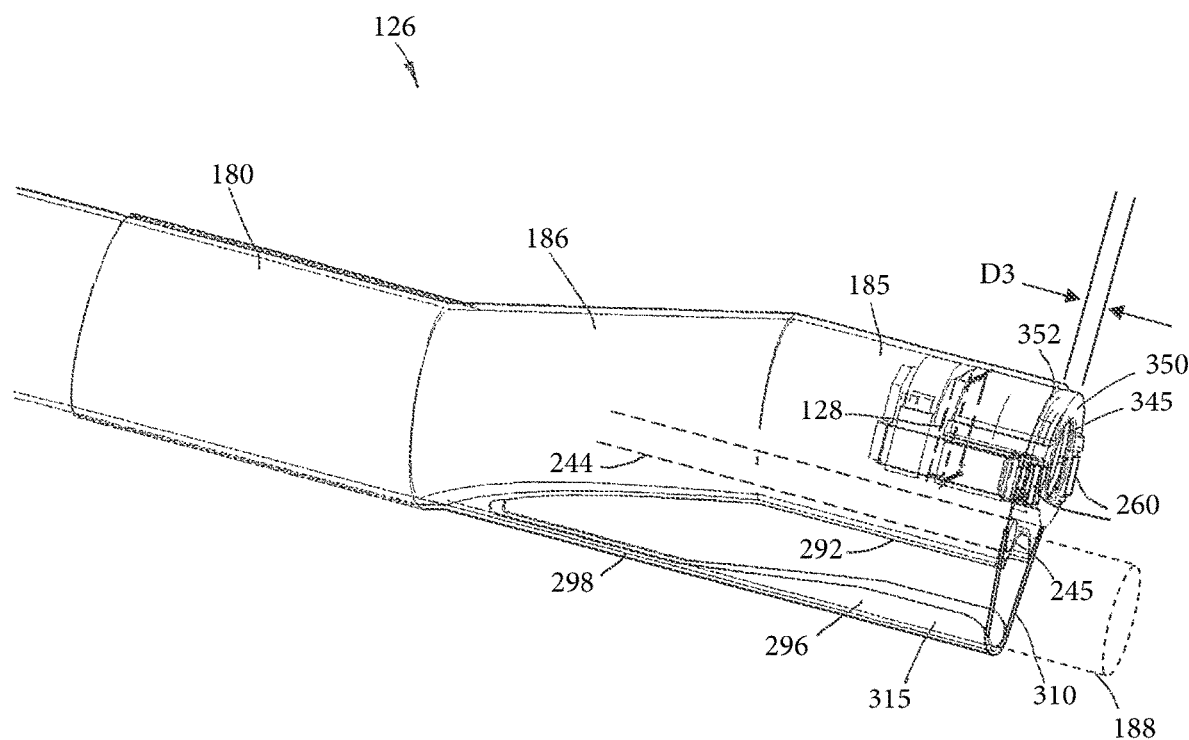
FIG. 8 is another view of the distal end of the endoscope shaft assembly of FIGS. 7A-7B showing the image sensor housing extending distally from the distal surface of the outer sleeve tip.

Now turning to FIG. 8, the image sensor 128 is carried in a sensor housing 340 that also carries a lens assembly 345 as is known in the art. In one variation, the housing 340 also carries one or more light emitters, in the variation shown in FIGS. 7A and 7B, two LEDs indicated at 260 are shown carried in opposing sides of the sensor housing 340. Of particular interest, the distalmost surface 350 of the lens assembly 345 and the LEDs 260 are disposed distally outward from the distal surface 352 of distal tip section 185 as shown in FIG. 8. It has been found that providing such a distalmost surface 350 of the lens assembly and the LEDs outwardly from the distal surface 352 of distal tip section 185 improves lighting from the LEDs 260 as well as improving the field of view of the image sensor 128. The distance indicated at D3 in FIG. 7 can range from 0.2 mm to 2.0 mm.

Now referring to FIG. 7A, another aspect of the invention comprises an optionally dedicated fluid pressure sensing channel 360 that extends through a thin wall sleeve (not shown) in the endoscope shaft 126. As can be seen in FIG. 7A, the distal end of the pressure sensing channel 360 is open in the distal surface 352 of the endoscope shaft 126. The pressure sensing channel 360 can extend to disposable pressure sensor in the handle housing 145 (not shown). Such a disposable pressure sensor then can have electrical leads coupled through the electrical connector 190A in the handle housing 145 thereby send electrical signals indicating pressure to the controller 110A (FIG. 1). Thus, in one aspect, the disposable endoscope component 125 carries a single-use pressure sensor coupled by a detachable connector to a remote controller 110A.

In one variation of a pressure sensing mechanism, referring to FIG. 7A, the wall of the pressure sensing channel 360 consists of a hydrophobic material, which can be any suitable polymer such as PFTE, having an interior diameter ranging from 0.25 mm to 2.5 mm. Often, the diameter of channel 360 is between 0.5 mm and 1.5 mm. It has been found that a hydrophobic surface in a pressure sensing channel 360 will prevent the migration of fluid into the channel and thereby trap an air column in the channel communicating with the pressure sensor. The compressibility of the air column in the pressure sensing channel 360 does not significantly affect the sensed pressure since the channel diameter is very small. In another variation, a metal sleeve can be coated with a hydrophobic surface or an ultrahydrophobic surface.

Now referring to FIGS. 1, 2 and 4, it can be seen that the handle component 120 has an angled pistol grip portion 192 with an axis 194 that is angled from 10° to 90° away from the axis 175 of the endoscope shaft 126. The grip portion 192 includes a finger or thumb-actuated control pad 122 that carries actuator buttons for operating all the functions of the treatment system, for example, including (i) operating the fluid management system 105, (ii) capturing images or videos from sensor 128, (iii) adjusting light intensity from the LEDs 260, etc. As described above, the control unit 108 typically carries the image processor 110B. However, the interior of the handle component 120 also could carry the image processor 110B or a processing component thereof.

FIG. 4 illustrated the handle component 120 and endoscope component 125 from a different angle where it can be seen that the grip portion 192 has a recessed channel 385 therein that is adapted to receive and lock in place the inflow and outflow tubing, 200A and 200B, so as to integrate the tubing set with the pistol grip 192 during use. This feature is important so that the inflow and outflow tubing will not interfere with operation of the endoscope component 125 or a tool introduced through the working channel 170. The pistol grip 192 can have a single recessed channel 385 to receive both the inflow and outflow tubing or two recessed channels for separately receiving the inflow tubing and the outflow tubing.

Figure 6:
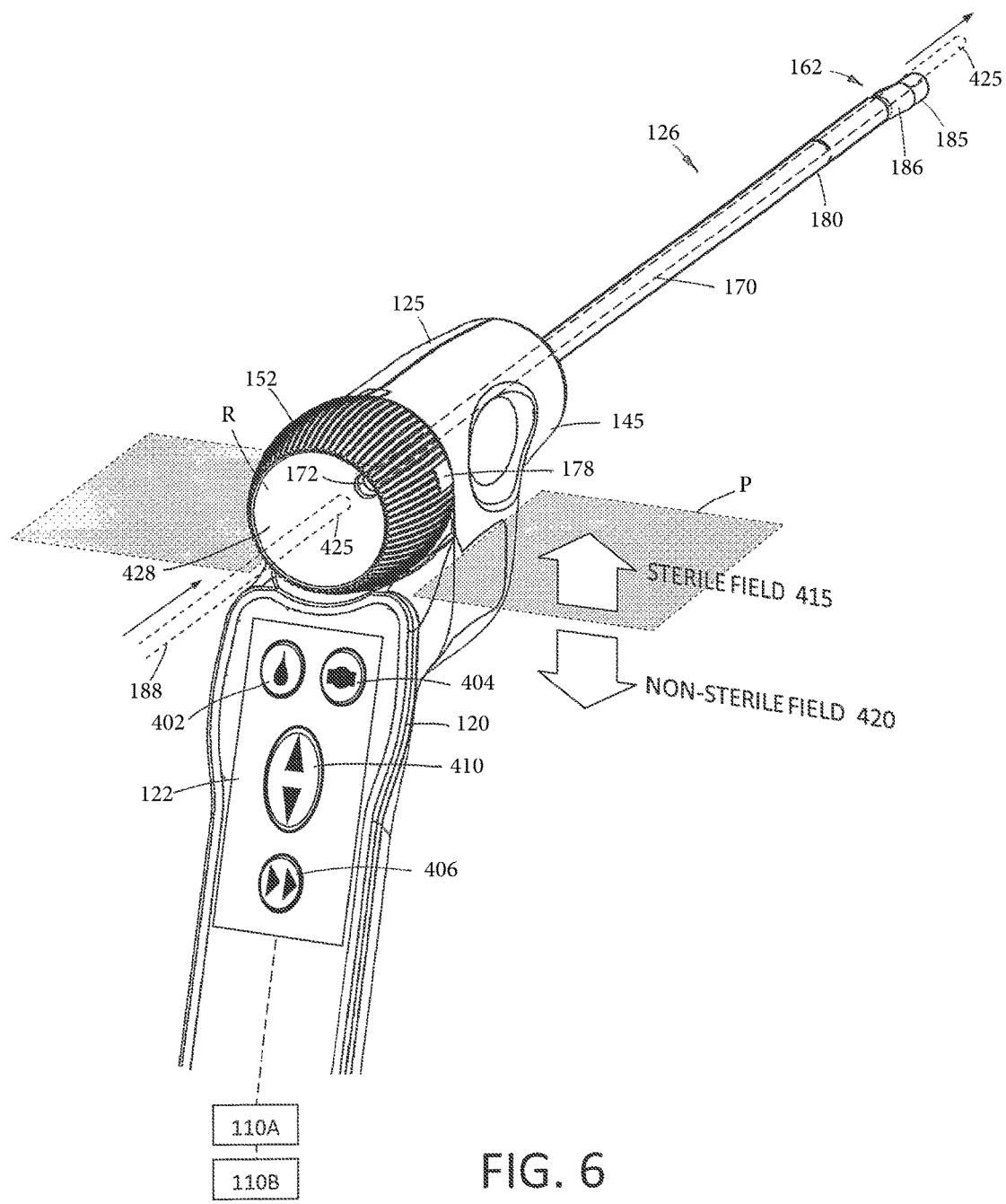
FIG. 6 is in an enlarged perspective view of the endoscopic viewing system of FIGS. 1 and 2 showing the finger-actuated control panel in the reusable handle component and the sterile and non-sterile fields of the components.

Now turning to FIG. 6, the enlarged view of the assembled handle component 120 and endoscope component 125 shows the control pad 122 with four actuator buttons or switches which are adapted to operate the system. In one variation, actuator 402 is adapted for turning on and off irrigation, or in other words actuating the fluid management system 105 to provide fluid inflow and fluid outflows. Actuator 404 is adapted for image or video capture. In a variation, momentary pressing the actuator 404 will capture a single image and longer pressure on the actuator will operate a video recording.

The actuator or scrolling button 406 has a scrolling function, wherein pressing the scrolling button 406 will cycle through various subsystems, wherein each subsystem then can be further adjusted by the central button or up/down actuator 410, which is adapted for increasing, decreasing or otherwise changing an operating parameter of any selected subsystem. In one example, the scrolling button 406 can be actuated to cycle through the following subsystems and features: (i) fluid inflow/outflow rate from the fluid management system 105; (ii) the set pressure which is to be maintained by fluid management system 105; (iii) fluid deficit alarm which is calculated by the fluid management system 105; (iv) optional selection of still image capture or video capture, and (v) LED light intensity. Then, after scrolling to select a subsystem, the physician can actuate the central up/down actuator 410 to adjust an operating parameter of the selected subsystem. As will be described further below, the selection of subsystems as well as the real-time operating parameters of each subsystem will be displayed on a video monitor or display 112 as shown in FIG. 1. Thus, it can be understood that the physician may operate the scrolling button 406 to scroll through and select any subsystem or feature while observing such as selection on the display 112, and then actuate the up/down actuator 410 to adjust an operating parameter which also can be observed on the display 112.

In another aspect of the invention, the controller 110A includes a control algorithm for operating the control pad 122 which provides a jump back to a default condition after the scroll button or actuator 406 has been used by the physician. For example, the default condition will be a selected default subsystem which is actuatable by the central up/down actuator 410. In one variation, the default subsystem is the fluid inflow/outflow rate, which may be the subsystem most commonly actuated by the physician to control fluid flow into and out of a working space. As described above, the physician may use the scrolling button 406 to select any subsystem for adjustment of an operating parameter. If, however, the physician does not continue to scroll between the various subsystems or change a parameter within a predetermined time interval, then the control algorithm will jump back to the default subsystem, which may be the fluid inflow/outflow rate. The predetermined time interval, or timeout, for the control algorithm to jump back to the default condition may be anywhere from 1 second to 10 seconds, more often between 2 seconds and 5 seconds.

Still referring to FIG. 6, the assembly of the handle component 120 with endoscope component 125 is shown with a plane P to illustrate the sterile field 415 and the non-sterile field 420 relative to the endoscope assembly. As can be understood, the disposable endoscope component 125 is sterilized and the physician or nurse would remove the component 125 from sterile packaging which would then define a sterile field 415. The endoscope component 125 then would be mated with the handle component 120 which defines the non-sterile field 420. In other variations (not shown), a plastic film or other plastic housing could cover the handle portion 120.

A method of the invention can also be understood from FIG. 6. It can be understood that the physician must insert the tool 188 into the working channel 170 in a manner that would ensure the sterility of the tool. As can be seen in FIG. 6, the grip 152 which is sterile has a large diameter recess R therein which tapers into the proximal port 172 of the working channel 170. In one variation, the diameter of the recess R is at least 15 mm and often greater than 20 mm. The depth of the recess can range from 5 mm to 20 mm or more. Thus, it can be understood that the physician can easily insert the distal end 425 of a tool 188 into the mouth of the large diameter recess R without any risk of contacting the non-sterile handle portion 120. Thereafter, the physician can move the tool distal end 425 distally over the surface 428 of the recess R and into and through the port 172 of the working channel 170. By using this method, the physician can be assured that the tool 188 will not contact the non-sterile field 420.

Figure 9:
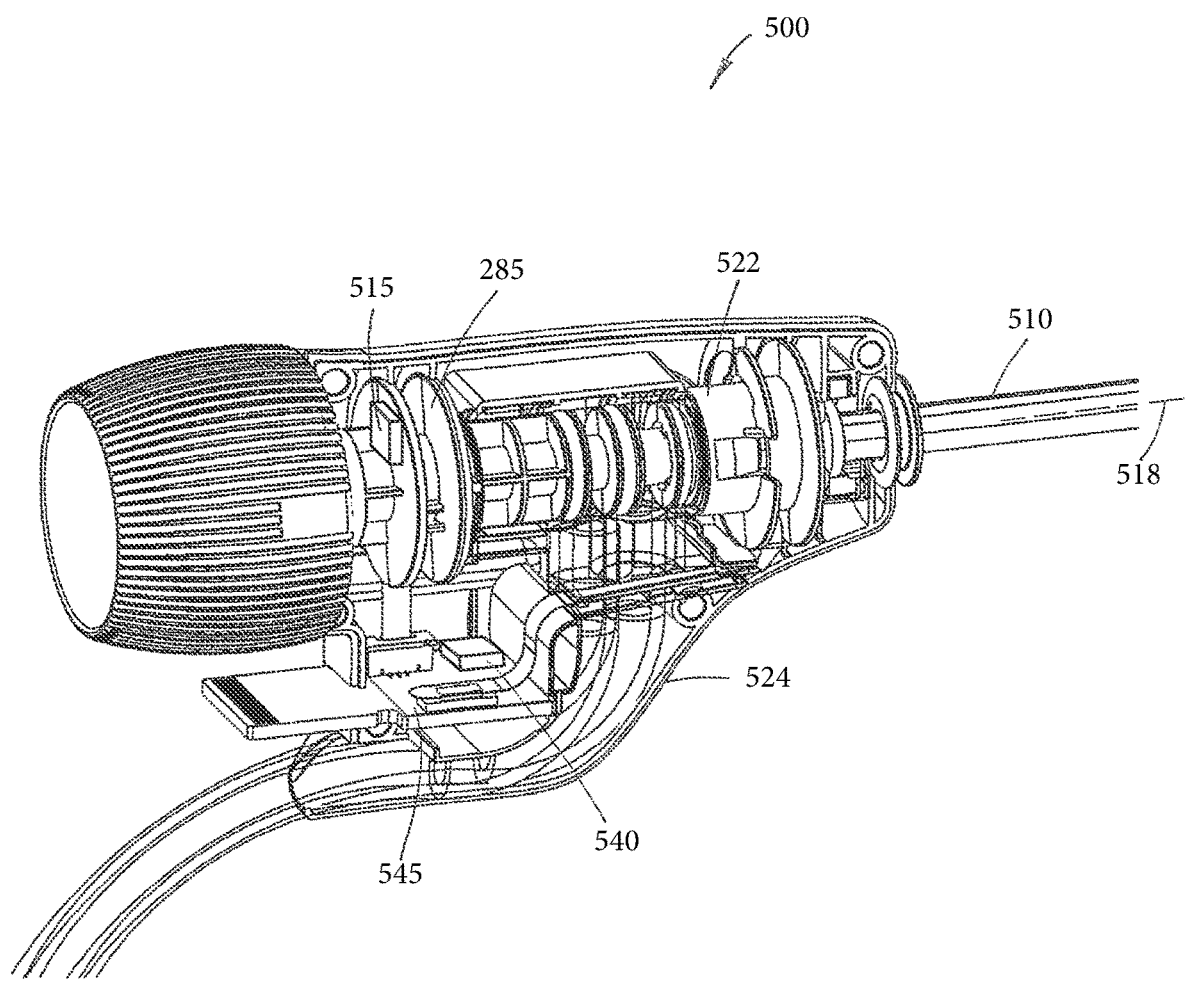
FIG. 9 is another view of the endoscope handle assembly which carries at least one accelerometer for image orientation.

Now turning to FIG. 9, another aspect of the invention is shown which relates to electronic mechanisms carried by the endoscope 500 for re-orienting the image on the display in response to rotation of the endoscope shaft 510 to ultimately provide an image-upright configuration on the display. In one variation, an accelerometer 515 (which can comprise an accelerometer gyroscope combination) is provided which can send signals to a controller and image processor related to rotation of the endoscope shaft 510. For example, an STmicro IIS2DH 3-axis accelerometer can be used or a 6-axis IMU (Inertial Motion Unit) with 3-accelerometer and 3-gyroscope axis such as an STmicro ISM330DLC can be used.

The image processor in the controller then can use the accelerometer signals to calculate a necessary amount of rotational correction for the image re-orientation. The calculation includes the degree of rotation of the shaft 510 relative to the longitudinal axis 518 of the shaft 510. The image is then electronically rotated to display on any video display or monitor can be carried by the handle of the device or most often is a remote display. Thus, the video image on the display can at all times be in an image-upright configuration for viewing by the physician.

As can be seen in FIG. 9, the accelerometer 515 is carried on the proximal spool 285 which is rotatable within the handle assembly 520. Thus, any rotation of the rotating component 522 independent of the handle 524 or rotation of the handle 524 relative to the longitudinal axis 518 of the shaft will be sensed by the accelerometer 515 to thus allow reorientation of the image on the display. In the variation of FIG. 9, a second accelerometer 540 is carried on the circuit board 545 which is fixed in the non-rotating handle 524. Thus, signals from this accelerometer 540 provide signals of rotation of the handle only. In one variation, signals from both accelerometers 515, 540 can be compared to determine rotation of the rotating component relative to the handle 524. In one aspect, signals from the second accelerometer 540 can be used if signals from the first accelerometer 515 fail for any reason. An alert on the display can indicate to the user if either the first or second accelerometer has failed to perform properly.

Figure 10:
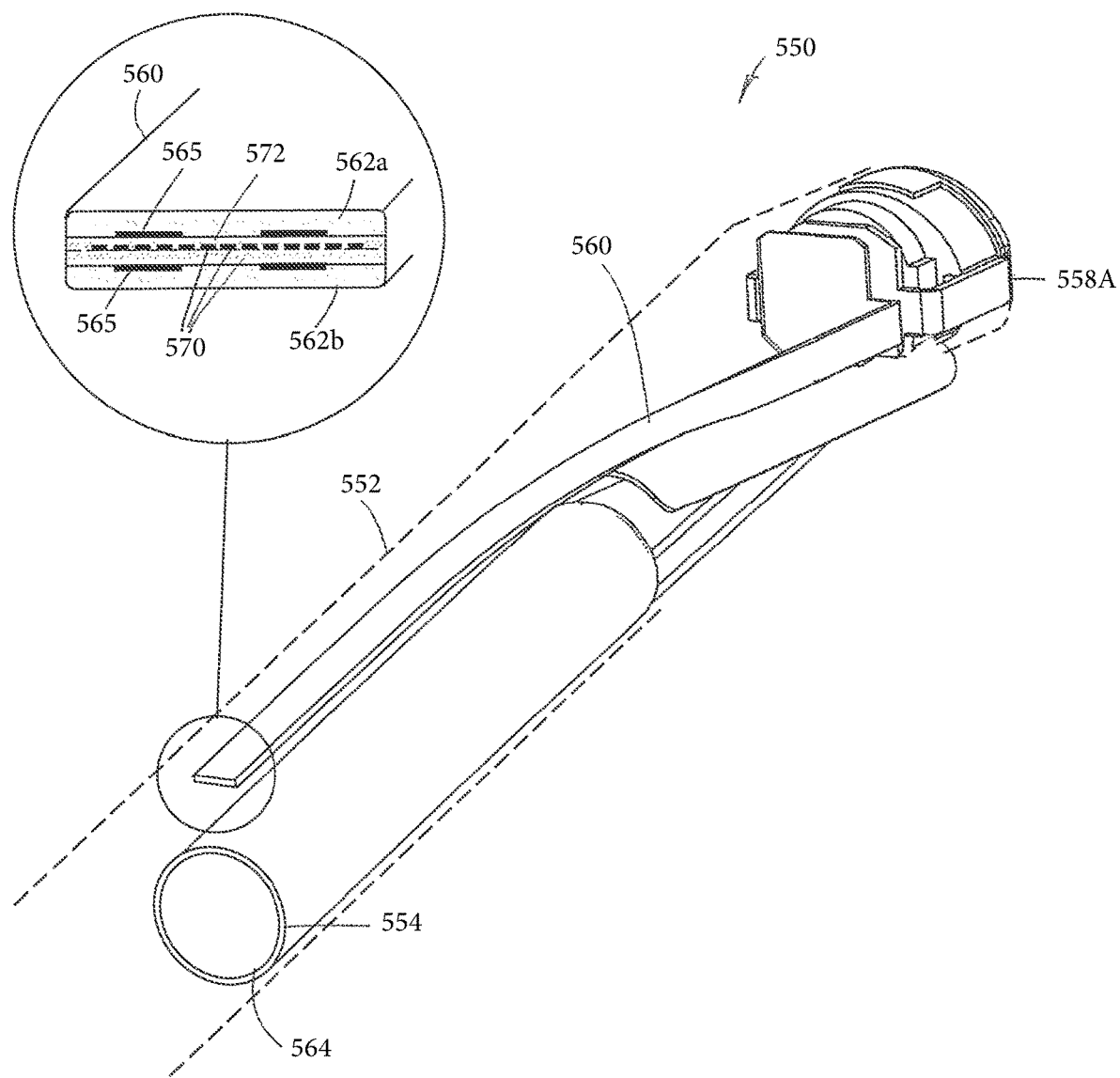
FIG. 10 is a de-constructed view of the endoscope working end showing a flex circuit configuration.
Figure 11:
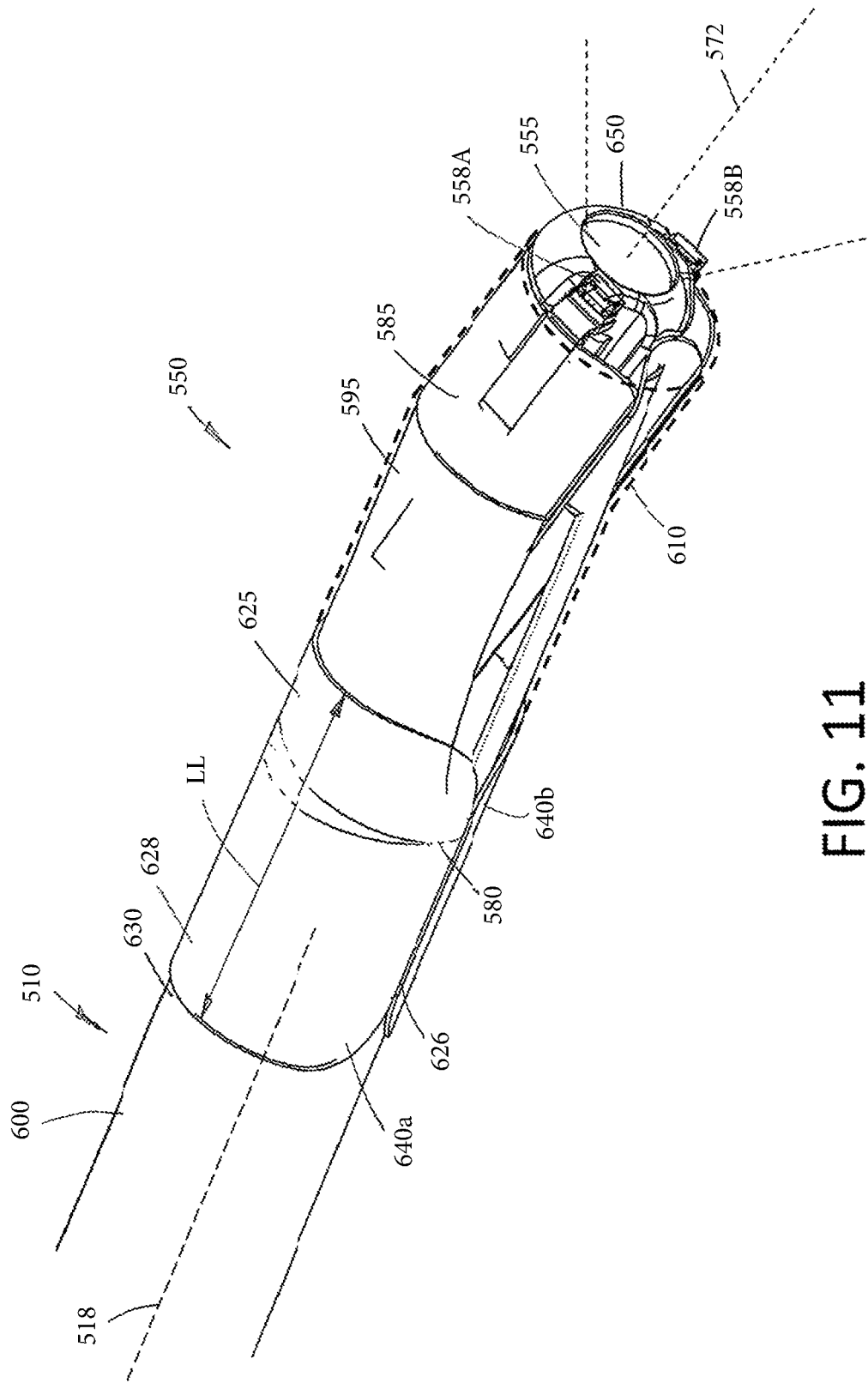
FIG. 11 is another view of the endoscope working end of FIG. 10.

FIGS. 10 and 11 illustrate another variation of an endoscope working end 550 which is similar to the previous embodiment. The thin-wall outer sleeve 552 is in phantom view in FIG. 10 and the thin-wall working channel sleeve 554 is shown. As described previously, electronic signals from the image sensor 555 (FIG. 11) as well as power for the image sensor and LEDs 558A and 558B are carried in a flex circuit 560 extending through the shaft 510 of the endoscope. Since the endoscope shaft 510 will be operating in a fluid environment, it has been found that significant RF shielding is needed around the signal-carrying electrical conductors in the flex circuit 560 to ensure that potential electrical devices introduced through the working channel 564 will not generate electrical fields that may interfere with signals carried in the flex circuit 560.

Thus, in one variation shown in FIG. 10, the flex circuit may be an edge-coupled stripline design where two outer dielectric layers 562a and 562b carry electrical conductors 565 (including ground planes) and are configured to function as a shield relative to the electric conductors 570 disposed in a middle layer 572 between the two outer layers 562a and 562b. In this variation, the plurality of electric conductors 570 disposed in the middle layer 572 are adapted to carry all the signals from the image sensor 555. Thus, the two outer layers 562a and 562b function as a shield to prevent any potential interference from electrical tools that might interfere with the signals carried by the interior conductors 570 in the middle layer 572.

In one variation, the signal carrying conductors 570 in the middle layer 572 are provided with a dielectric insulator layer on both sides that has a thickness of at least 0.0127 mm (0.0005"), at least 0.0254 mm (0.001") or at least 0.0508 mm (0.002"). The insulator layers can be any suitable power material such Kapton.

In some variations, the number of electrical conductors 570 that carry image signals in the middle layer 772 can vary from 4 to 24 or more and typically range from 12 to 20 conductors. In this variation, the electrical leads to the LEDs 558A and 558B are also carried in the middle layer 572 which could be subject to interference from electrical tool. Thus, providing the electrical leads and signal conductors in the middle layer 572 in the stripline design allows for an overall flex circuit 560 that is thinner and more flexible than other configurations that provide adequate RF shielding.

Figure 12A:
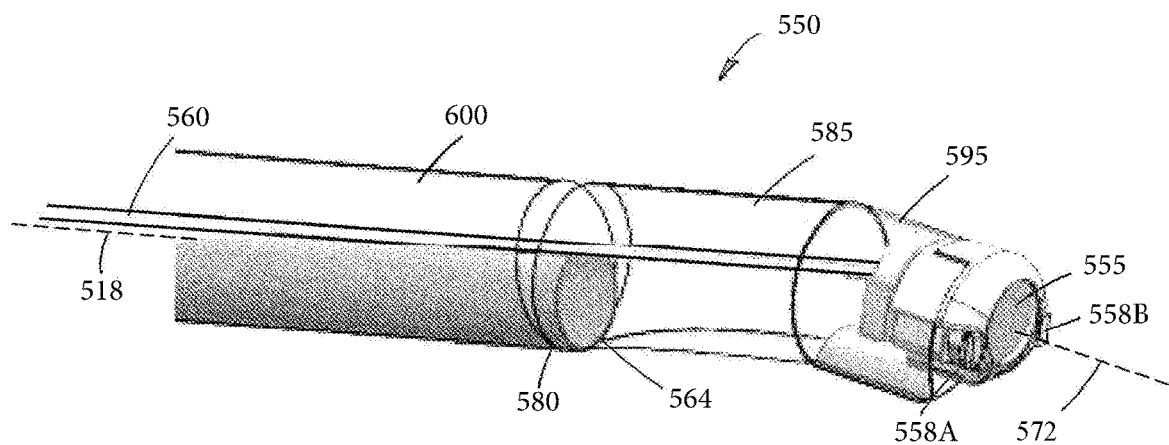
FIG. 12A is another view of the endoscope working end of FIG. 11 in a non-articulated configuration.
Figure 12B:
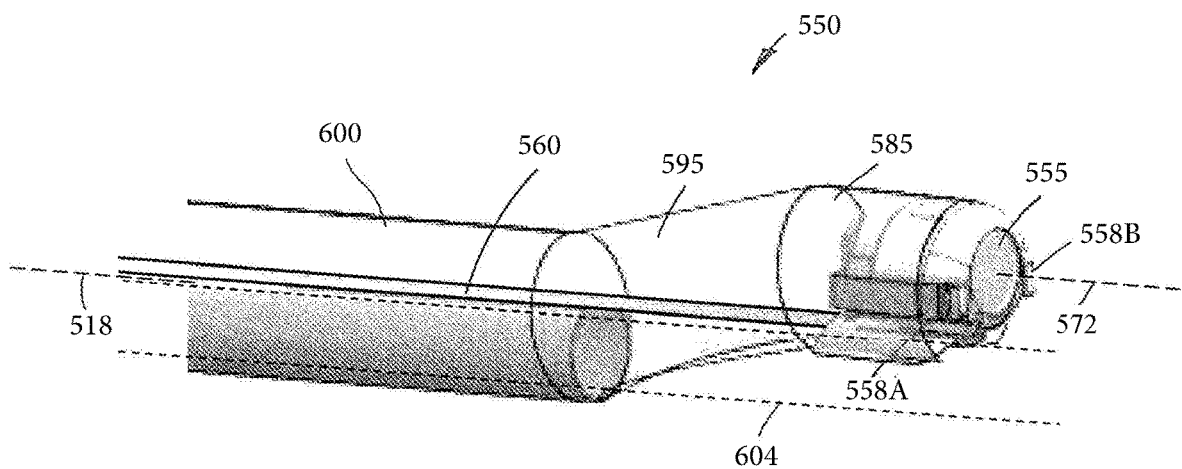
FIG. 12B is another view of the endoscope working end of FIG. 112A in an articulated configuration.

Now turning to FIGS. 11-13, the endoscope shaft working end 550 is similar to that of FIGS. 7A and 7B. In the variation of FIG. 11, the shaft working 550 end has a secondary flexible hinge portion 580 which allows for changing the angle of the field of view FOV of the image sensor 555 about its axis 572. For introduction into a working site in the patient's body, the working end 550 of the shaft 510 has a distal segment 585 that has an axis 588 that is angled relative to the longitudinal axis 590 of the shaft 510 at a selected angle which can be from 5° to 30°. It can be seen in FIG. 11 that a second or intermediate segment 595 of the working end 550 includes a living hinge portion 580 which allows it to flex relative to the proximal shaft segment 600. The intermediate segment 595 and distal segment 585 are fixed together at an angle which can be seen in FIGS. 11 and 12A. The mechanism for actuating the distal segment 585 and intermediate segment 595 to a flexed position (see FIG. 12B) consists of inserting an elongated tool body or shaft 604 through the working channel 564 as described previously.

FIGS. 12A and 12B are schematic transparent views of the working end 550 of FIG. 11 showing the interior working channel 564 and the proximal shaft segment 600, the intermediate shaft segment 595 and the distal shaft segment 585. In FIG. 12 B, it can be seen that the elongated tool body 604 (phantom view) has been inserted through the working channel 564 which causes multiple effects. First, as described previously, the elongated tool shaft 604 stretches the resilient silicone sleeve 610 around the working end 550 (FIG. 11) to expand the working channel 564 from a collapsed condition to an expanded condition. At the same time, the introduction of the tool shaft 604 through the working channel 564 flexes the proximal hinge 580 at the proximal end of the intermediate segment 595 to cause the intermediate and distal segments 595 and 585 to flex away from the repose position (FIG. 12A) to a tensioned position (FIG. 12B) wherein the axis 588 of the image sensor 555 is parallel to the longitudinal axis 518 of the proximal shaft portion 600. In this flexed position of FIG. 12B, the image sensor 555 then is aligned with the longitudinal axis 518 of the shaft and the sensor axis 572 and the angle of the field of view FOV then can be 0° relative to the longitudinal axis 518 of the shaft.

In this variation shown in FIG. 11, it can be seen that the tensioning support sleeve 625 is shown which partially surrounds the proximal endoscope shaft portion 600 and sleeve segment 595. More in particular, the support sleeve 625 has an upper surface 628 that is fixed to the adjacent upper surface 630 of the proximal shaft portion 600. The support sleeve 625 has a longitudinal discontinuity 626 therein and the sleeve extends around the shaft from about 200° to 360°. It can further be seen in FIG. 11 that the support sleeve with a length LL which extends over a portion of the proximal shaft 600 and over a portion of the intermediate sleeve 595. As can be seen in FIGS. 11 and 13, the interior portion of the support sleeve 625 has the longitudinal gap or discontinuity 626 which allows the side portions 640a and 640b to be flexed outwardly when an elongated tool shaft 604 is introduced through the working channel 564. In this aspect, the support sleeve 625 functions as a spring which urges the support sleeve 625 radially inwardly to return the endoscope shaft 510 to a straight configuration when the tool shaft 604 is removed from the working channel 564.

In another aspect of the invention referring to the exploded view of FIG. 13, it can be seen that the distal end of the distal shaft segment 595 includes a housing 650 that carries both the image sensor 555 and first and second LEDs 558A and 558B. The housing 650 can be molded out of any suitable polymer and includes means for providing flex circuit connections to both the image sensor 550 and the LEDs. An upper guide surface 655 is coupled to the sensor housing 650 to provide a sliding interface against which the tool shaft 604 can push and deflect the distal segment 595 and sensor housing 650. A lower guide surface 660 is coupled by a flexible element 664 to the working channel sleeve 554 to provide a sliding interface against which the tool shaft 604 can open the working channel 564 without contacting the silicone sleeve 610 (see FIG. 11).

Now turning to FIGS. 14 through 17B, another variation of components of an endoscope working end 700 is shown which includes a distal housing 704 that carries an image sensor 705 (FIG. 17B) and lens stack 708 together with a flex circuit 710 that is configured for coupling to the image sensor as well as two LEDs 715A and 715B. In one aspect of the invention, the elongated flex circuit 710 is adapted to be carried in the interior of the endoscope shaft or sleeve 720 in a channel that can be used for fluid inflows and fluid outflows. Thus, the flex circuit 710 and its connections to the image sensor and LEDs are entirely insulated to allow for its use when submerged in such fluid flows.

As can be understood with reference to FIGS. 3A-3B, 5, 10, 12A-12B and 13, previous variations of the endoscope of the invention are shown with a flat flex circuit extending through a fluid flow channel in the elongated shaft of the endoscope. It has been found that typical insulator layers on flex circuits are suited for operating in an air environment where electrical coupling through the surface insulator is not problematic. However, it has been found to be challenging when such a flex circuit carries sensitive conductors from an image sensor and when the flex circuit is submerged in a fluid environment and in particular in a conductive saline fluid inflow or outflow. In one variation, an improved endoscope includes an integrated fluid management system so the flex circuit is effectively insulated to prevent noise in the image sensor conductors.

Figure 14:
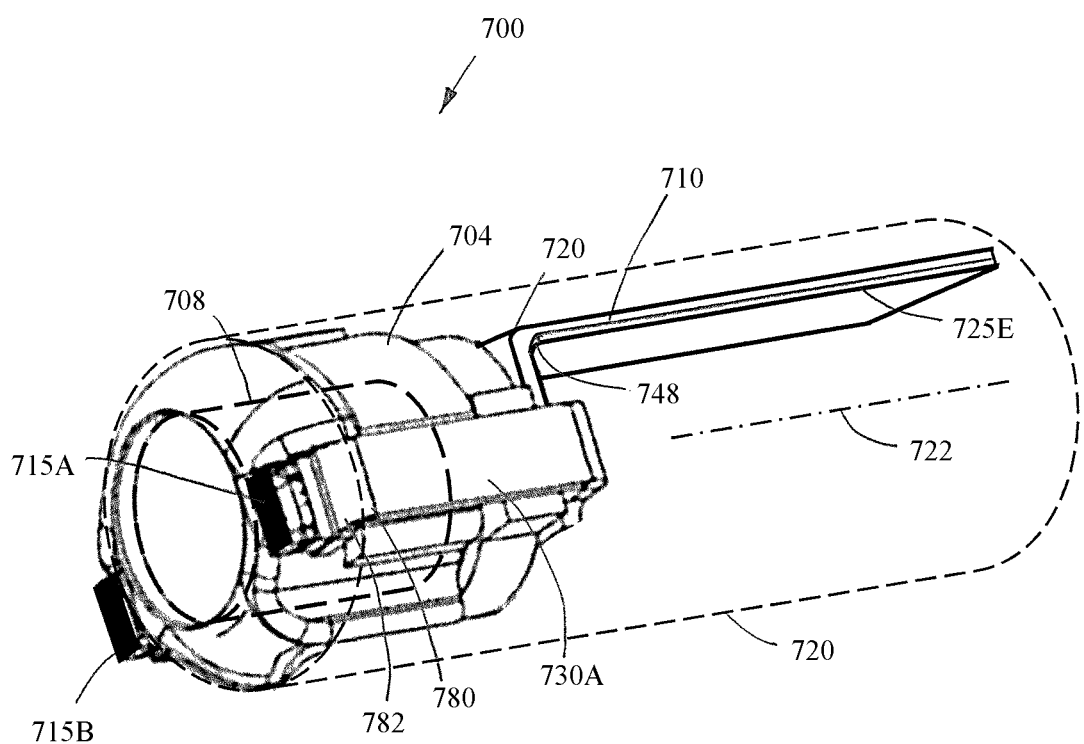
FIG. 14 is perspective view of a housing and lens assembly in the distal end of an endoscope similar to that of FIGS. 10, 11, 12A and 12B showing a single flex circuit with multiple bends or folds therein for coupling electrical leads to the image sensor and to two LEDs.
Figure 15:
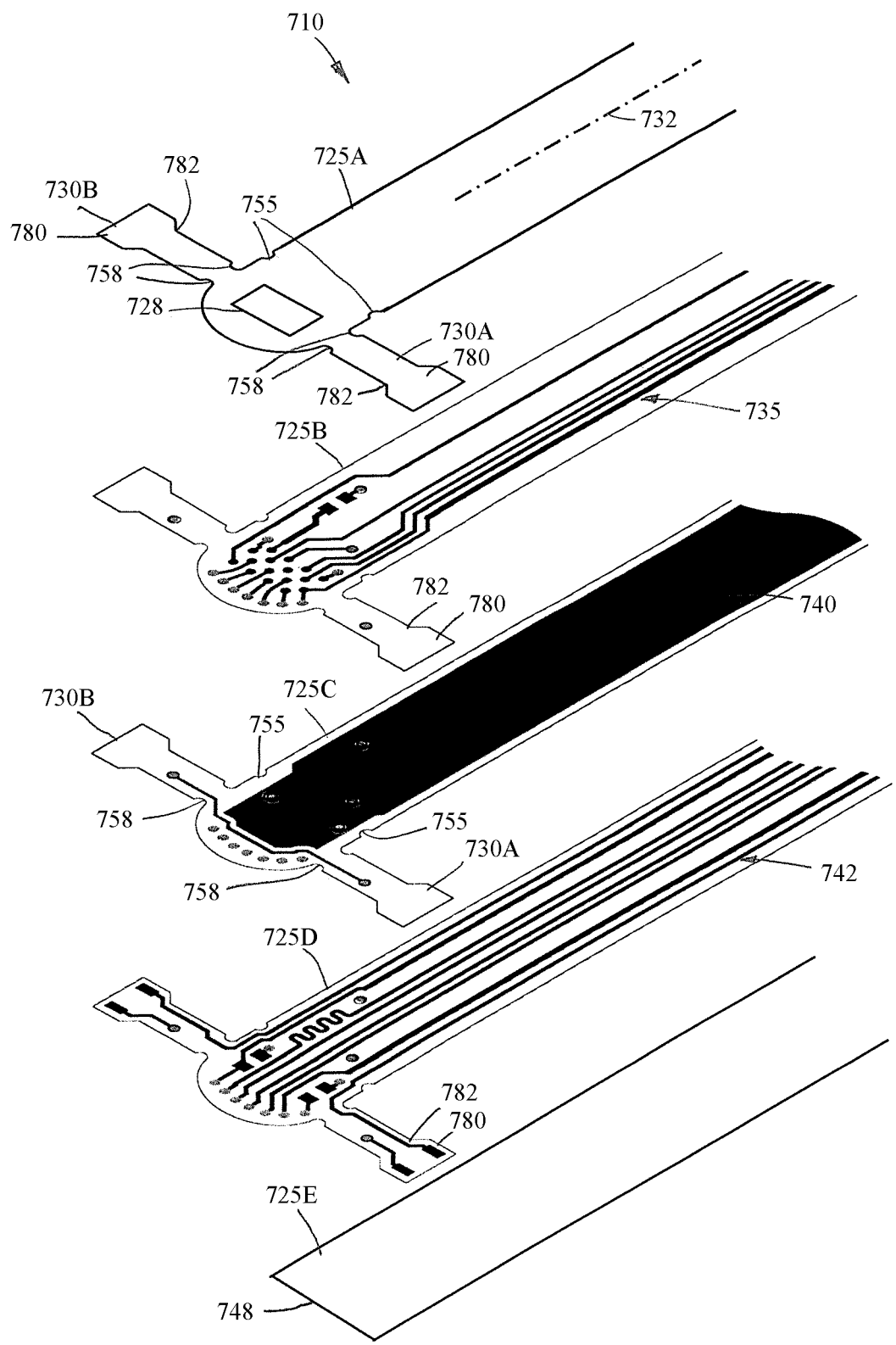
FIG. 15 is a perspective view of the distal portion of the flex circuit

Referring to FIG. 15, the first or superior insulator layer 725A and the last or inferior insulator layer 725E of the flex circuit 710 comprise dielectric layers that are thick enough to prevent capacitive coupling therethrough to the image sensor conductors indicated at 742 in FIG. 15. In one variation, the superior and inferior dielectric layers 725A and 725E each comprise a polymeric layer having a thickness of at least 0.002". In other variations, the dielectric layers each are at least 0.003" or at least 0.004". In one variation, the dielectric layer can be a polyamide such as Kapton®. In general, a flexible circuit for an endoscope used in a fluid environment corresponding to the invention comprises an elongate flexible circuit extending in a planar shape to a distal end, an image sensor operatively coupled to a surface of the flex circuit with a first arrangement of electrical conductors therein, an illumination source operatively coupled to a surface of the flex circuit with second arrangement of electrical conductors therein, where said first arrangement of electrical conductors is disposed in an interior of the flex circuit with superior and inferior dielectric layers sufficient to prevent electrical coupling through said dielectric layers to thereby prevent interference with image sensor signals carried by said first arrangement of electrical conductors. FIG. 14 is perspective view of the housing 704 and lens assembly or stack 708 in the distal working end 700 of an endoscope similar to that of FIGS. 10, 11, 12A and 12B. It can be seen that a single flex circuit 710 is shaped for folding to allow the image sensor 705 and the LEDs 715A, 715B to be oriented distally or aligned with the longitudinal axis 722 of the endoscope shaft. Thus, the multiple electrical leads to the image sensor 705 and to two LEDs can be provided in a single flex circuit which conserves space in the endoscope shaft which is critically important.

Figure 17A:
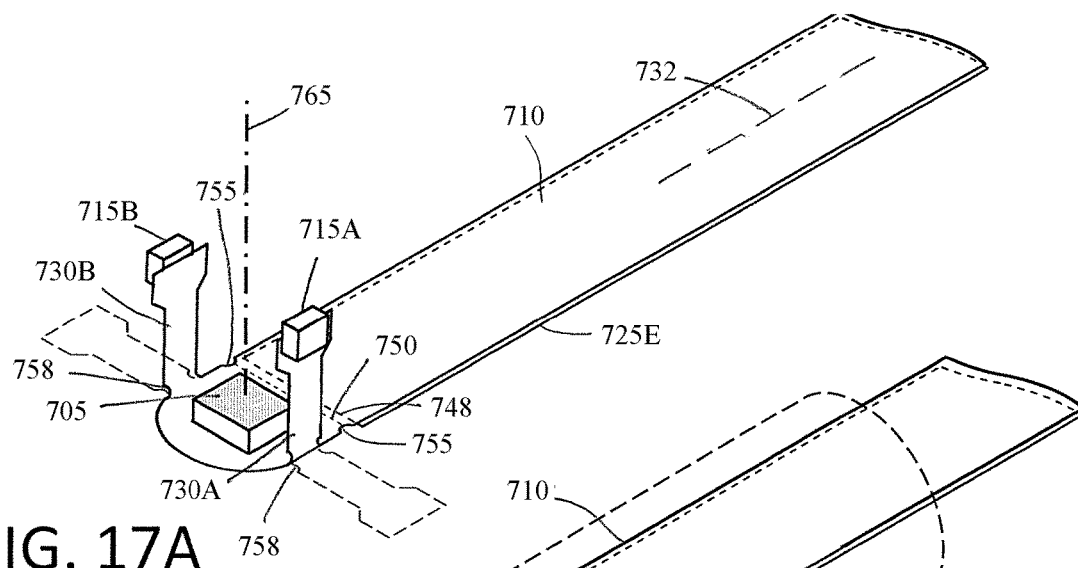
FIG. 17A is a perspective view of the distal portion of the flex circuit FIG. 15 after a first folding step where segments of the flex circuit folded after coupling to the LEDs to orient light emission from the LEDs in a selected direction.

FIG. 15 is a perspective view of the distal portion of the flex circuit 710 of FIG. 14 in an exploded view showing the five thin film layers that comprise of the flex circuit 710 in a planar form before bonding into the single component. The first layer 725A or layer 1 comprises a thin-film insulator layer which covers the electrical leads in the second layer 725B or layer 2. A central portion of the distal end of the layer 1 indicted at 725A includes an open port 728 that exposes the electrical leads in layer 2 (725B) for coupling to the image sensor 705 as shown in FIG. 17A. It can be seen in FIG. 15 that layers 1 through 4 of the flex circuit 710 are configured with first and second legs 730A and 730B that extend laterally or perpendicular to the axis 732 of the flex circuit which are adapted to couple to the LEDs as will be described below.

Figure 17B:
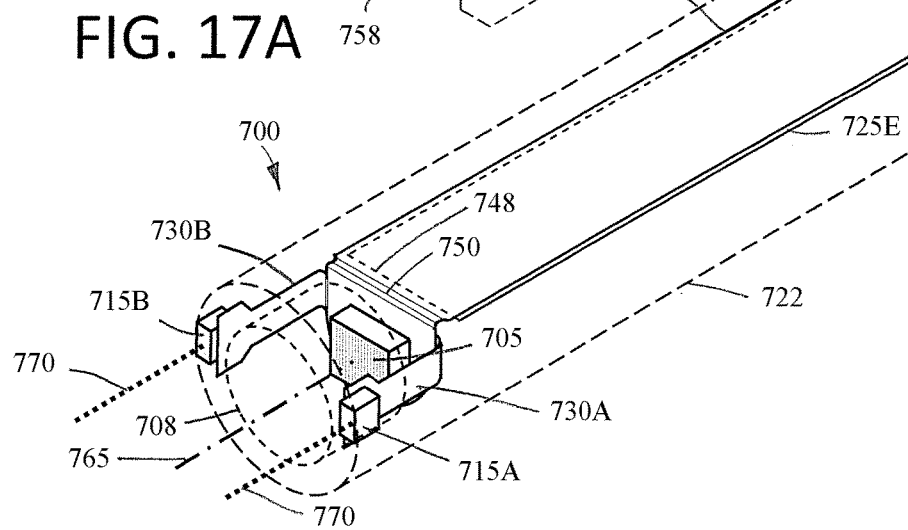
FIG. 17B is perspective view of the distal portion of the flex circuit FIG. 17A after a second folding step where a portion of the flex circuit is folded orient the image sensor field of view in the distal direction relative to the shaft of the endoscope.

The second layer 725B or layer 2 of the flex circuit carries a plurality of electrical leads 735 that extend to the image sensor 705. Layer 3 indicated at 725C of the flex circuit carries a planar ground element 740. Layer 4 indicated at 725D of the flex circuit carries additional electrical leads 742 coupled to the image sensor 705 as well as leads that couple the two LEDs in a series connection. Layer 5 indicated at 725E of the flex circuit 710 does not have a shape with laterally-extending legs 730A and 730B corresponding to the shape of the layers 1 through 4. Layer 5 is configured as a stiffener layer with a distal end 748 that defines a bending region 750 extending transversely across the flex circuit 710 to provide a bending line for layers 1 through 4 when bonded together (FIGS. 17A-17B).

In FIG. 15, it can be seen that layers 1 through 4 (725A-725D) include notch features for inducing bending of the flex circuit at selected locations. More in particular, notch features 755 provided on either side of the flex circuit 710 define a transverse line to induce bending of the flex circuit perpendicular to the longitudinal axis 732 as can be seen in FIGS. 17A and 17B. The laterally-extending legs or segments 730A and 730B also include notches 758 which are adapted to induce bending of such laterally-extending segments as also can be seen in FIGS. 17A and 17B.

Figure 16:
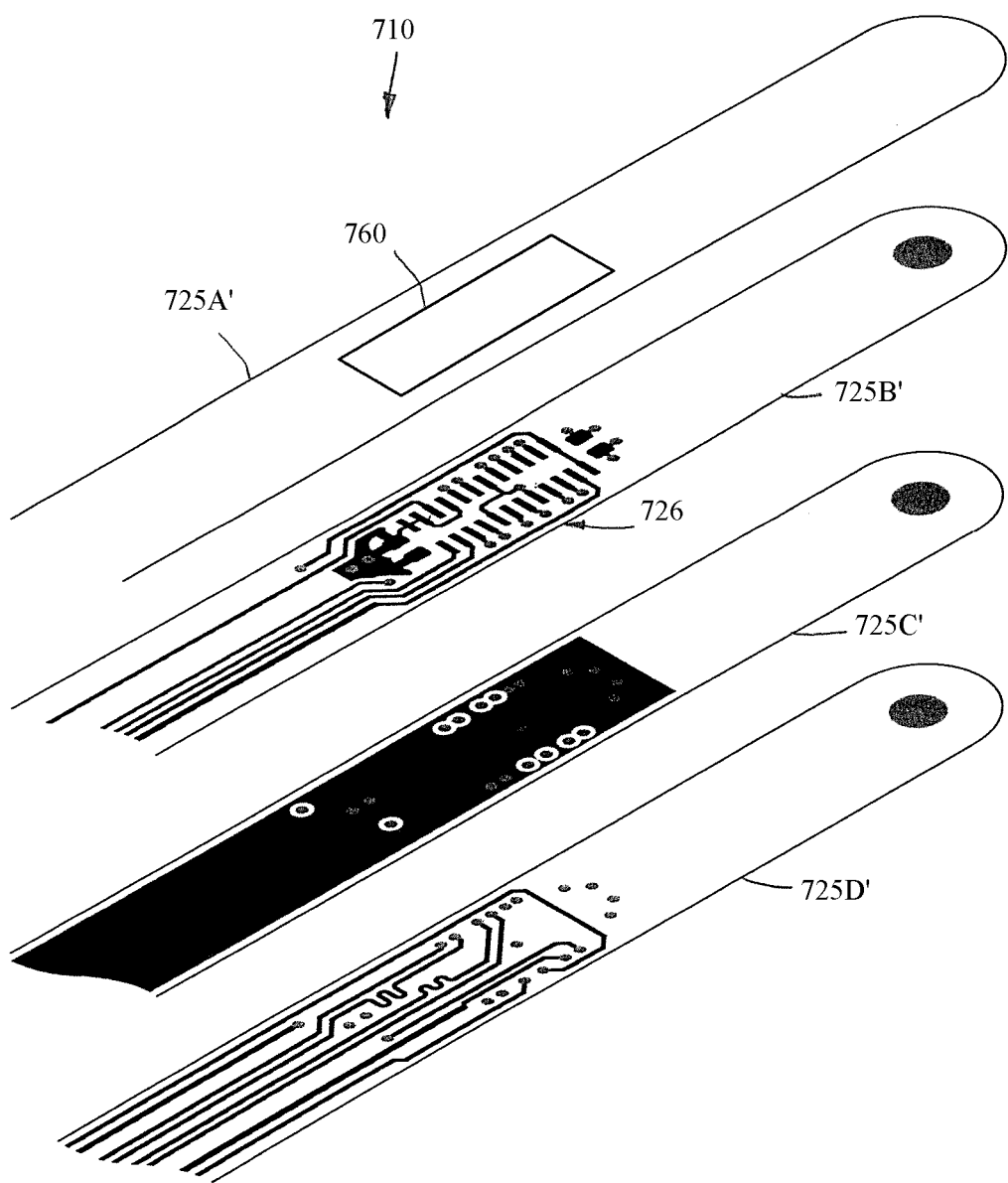
FIG. 16 is perspective view of the proximal portion of the flex circuit FIG. 15 showing the electrical leads that couple to the circuit board in the endoscope handle.

FIG. 16 shows the proximal ends of layers 1 through 4 (725A'-725D') of the flex circuit 710 in an exploded view with layer 1 (725A') having an open port 760 to expose the electrical connection points 762 in layer 2 (725B') which are adapted for coupling to a circuit board in the endoscope handle (not shown).

FIG. 17A is a perspective view of the distal portion of the flex circuit 710 of FIG. 15 showing the image sensor 705 and the LEDs 715A, 715B coupled to the flex circuit. In addition, it can be seen that the laterally-extending segments 730A and 730B are folded 90° away from the planar shape of the flex circuit as in its manufactured form shown in FIG. 15. The axis 765 of the field of view (FOV) of the image sensor is also shown. FIG. 17B then shows the transverse bending of the flex circuit 710 which then orients the axis 765 of the image sensor's field of view and the light transmission axes 770 of the LEDs in the distal direction. Thus, FIG. 17B is a schematic view of the components in the working end 700 of FIG. 14 where FIG. 17B does not show the lens housing 704 or the lens stack 708 with the outer sleeve 720 in phantom view. Referring to FIG. 14, it should be appreciated that the outer or distal tips 780 of the laterally extending segments 730A and 730B can be folded inwardly at point 782 (FIGS. 14 and 15) to attach to the proximal surface of the LEDs 715A, 715B or can be adapted to couple to the side of the LEDs or a circuit component attached to the LEDS as in FIGS. 17A and 17B.

In general, a flex circuit for an endoscope corresponding to the invention comprises an elongated flexible circuit manufactured to extend in a planar shape to a distal end having first and second flex elements adapted to bend away from the planar shape, an image sensor having a field of view (FOV) axis operatively coupled to a surface of the first flex element, and an LED with a light axis operatively coupled to a surface of the second flex element, wherein the first and second flex elements are capable of bending away from the planar shape to a non-planar shape for coupling to an endoscope shaft or housing where the FOV axis and light axis are in a distal-facing orientation after bending. It is understood that variations can employ any illumination source in addition to, replacing, the LED.

In another aspect, a flexible circuit assembly of the invention comprises an elongated flexible circuit member, an image sensor and at least one LED coupled to a distal portion of the flexible circuit member in a first spaced apart configuration, wherein said distal portion is configured for deformation or folding to dispose the image sensor and the at least one LED in a second spaced apart configuration for coupling to a distal housing of an elongated endoscope shaft that carries a lens or lens stack for the image sensor.

In another aspect a flexible circuit of the invention comprises an elongated flat flexible circuit member extending in a plane from a proximal end to a distal end and an image sensor operatively coupled to a first surface of the flexible circuit member where the sensor field of view is orthogonal to said first surface wherein a distal portion of the flexible circuit member carrying the image sensor is configured for flexing away from said plane for coupling to a distal portion of an elongated endoscope shaft to thereby re-orient the sensor field of view at an angle relative to the plane of the flex circuit member.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

What is claimed is:

1. An endoscope, comprising:
   an endoscope shaft having a longitudinal axis and a working channel therein;
   an elongated flex circuit extending in a planar shape to a distal end having first and second legs adapted to bend away from the planar shape;
   an image sensor with a field of view axis operatively coupled to a surface of the first flex leg;
   an illumination source with a light axis operatively coupled to a surface of the second flex leg;
   wherein the working channel is configured such that upon advancement of a tool through the working channel, the endoscope shaft flexes such that the image sensor transitions from a repose position to a tensioned position;
   wherein in the repose position the image sensor is at an angle relative to the longitudinal axis;
   wherein in the tensioned position the image sensor is parallel to the longitudinal axis;
   wherein the elongate flex circuit is outside of the working channel;
   wherein the first and second legs are capable of bending away from the planar shape to a non-planar shape for coupling to an endoscope shaft where the field of view axis and light axis are in a distal-facing orientation; and
   wherein the image sensor has a plurality of electrical contacts coupled to corresponding a first arrangement of electrical conductors in the flex circuit; and
   wherein said first arrangement of electrical conductors are disposed in one or more middle layers of the flex circuit, wherein the first arrangement of electrical conductors are spaced apart within the one or more middle layers, wherein superior and inferior dielectric layers surround the one or more middle layers and are sufficient to prevent electrical coupling through said dielectric layers to thereby prevent interference with image sensor signals carried by said first arrangement of electrical conductors, wherein the superior dielectric layer and the inferior dielectric layer each comprise a second arrangement of electrical conductors, wherein the one or more middle layers comprise first and second legs extending laterally to a longitudinal axis of the flex circuit and are coupled to the illumination source, wherein the first and second legs comprise notches adapted to induce bending of the first and second legs.

2. The endoscope of claim 1, wherein the superior and inferior dielectric layers each comprise a polymeric layer having a thickness of at least 0.002".

3. The endoscope of claim 1, wherein the superior and inferior dielectric layers comprise a polyamide.

4. The endoscope of claim 1, wherein the superior and inferior dielectric layers each comprise a polymeric layer having a thickness of at least 0.003".

5. The endoscope of claim 1, wherein the superior and inferior dielectric layers each comprise a polymeric layer having a thickness of at least 0.004".

6. The endoscope of claim 1, wherein said second arrangement of electrical conductors carried by the superior dielectric layer and the inferior dielectric layer prevent electrical coupling therethrough relative to the one or more middle layers.

7. The endoscope of claim 1, wherein the image sensor and the illumination source are coupled to a distal portion of the flex circuit in a first repose spaced apart configuration and is configured for deformation to dispose the image sensor and illumination source in a second spaced apart configuration for coupling to a distal portion of an elongated endoscope shaft.

8. The endoscope of claim 7, wherein the flex circuit has a planar shape in said first configuration and a non-planar shape in said second configuration.

9. The endoscope of claim 8, wherein a first leg of the flex circuit carrying the image sensor is configured for deformation from the planar shape to dispose the image sensor adjacent a proximal end of a lens assembly carried by the endoscope shaft.

10. The endoscope of claim 9, wherein a second leg of the flex circuit carrying the illumination source is configured for deformation to dispose the illumination source proximate to a distal end of the lens assembly.

11. The endoscope of claim 10, wherein the first leg includes a first flex region with increased flexibility for flexing away from said planar shape.

12. The endoscope of claim 10, wherein the second leg includes a second flex region with increased flexibility for flexing away from said planar shape.

* * * * *